US008784901B2

(12) United States Patent
Karagoezian

(10) Patent No.: US 8,784,901 B2
(45) Date of Patent: Jul. 22, 2014

(54) SYNERGISTIC ANTIMICROBIAL PREPARATIONS CONTAINING CHLORITE AND HYDROGEN PEROXIDE

(71) Applicant: S.K. Pharmaceuticals, Inc., San Juan Capistrano, CA (US)

(72) Inventor: Hampar L. Karagoezian, San Juan Capistrano, CA (US)

(73) Assignee: S.K. Pharmaceuticals, Inc., San Juan Capistrano, CA (US)

( * ) Notice: Subject to any disclaimer, the term of this patent is extended or adjusted under 35 U.S.C. 154(b) by 0 days.

(21) Appl. No.: 14/145,126

(22) Filed: Dec. 31, 2013

(65) Prior Publication Data

US 2014/0127319 A1 May 8, 2014

Related U.S. Application Data

(60) Division of application No. 13/658,609, filed on Oct. 23, 2012, which is a continuation of application No. 12/879,989, filed on Sep. 10, 2010, now abandoned, which is a division of application No. 12/874,443, filed on Sep. 2, 2010, now Pat. No. 8,460,701, which is a continuation of application No. 11/633,355, filed on Dec. 4, 2006, now abandoned, which is a continuation-in-part of application No. 10/614,646, filed on Jul. 7, 2003, now abandoned, which is a continuation-in-part of application No. 09/911,638, filed on Jul. 23, 2001, now Pat. No. 6,592,907, which is a continuation-in-part of application No. 09/412,174, filed on Oct. 4, 1999, now abandoned.

(51) Int. Cl.
*A61K 33/40* (2006.01)
*A61K 33/20* (2006.01)

(52) U.S. Cl.
CPC .............. *A61K 33/40* (2013.01); *A61K 33/20* (2013.01)
USPC .......... 424/661; 424/78.04; 424/616; 424/613

(58) Field of Classification Search
CPC .............................. A01N 59/00; C01B 11/10
USPC ........................................................ 424/601
See application file for complete search history.

(56) References Cited

U.S. PATENT DOCUMENTS

| | | |
|---|---|---|
| 2,701,781 A | 2/1955 | De Guevara et al. |
| 3,271,242 A | 9/1966 | McNicholas et al. |
| 3,585,147 A | 6/1971 | Gordon |
| 3,920,810 A | 11/1975 | Rankin |
| 4,250,269 A | 2/1981 | Buckman et al. |
| 4,317,814 A | 3/1982 | Laso |
| RE31,779 E | 12/1984 | Alliger |
| 4,499,077 A | 2/1985 | Stockel et al. |
| 4,574,084 A * | 3/1986 | Berger .................... 424/601 |
| 4,574,804 A | 3/1986 | Kurwa |
| 4,585,482 A | 4/1986 | Tice et al. |
| 4,654,208 A | 3/1987 | Stockel et al. |
| 4,670,185 A | 6/1987 | Fujiwara |
| 4,756,844 A | 7/1988 | Walles et al. |
| 4,855,135 A | 8/1989 | Ratcliff |
| 4,880,638 A | 11/1989 | Gorden |
| 4,891,216 A | 1/1990 | Kross |
| 4,956,348 A | 9/1990 | Gilbard et al. |
| 4,978,535 A | 12/1990 | Ratcliff |
| 4,997,626 A | 3/1991 | Dziabo et al. |
| 5,009,895 A | 4/1991 | Lui |
| 5,135,623 A | 8/1992 | Dziabo et al. |
| 5,145,644 A | 9/1992 | Park et al. |
| 5,152,912 A | 10/1992 | Dziabo et al. |
| 5,225,055 A | 7/1993 | Sibley et al. |
| 5,246,662 A | 9/1993 | Ridgley et al. |
| 5,270,002 A | 12/1993 | Neff et al. |
| 5,279,673 A | 1/1994 | Dziabo et al. |
| 5,281,353 A | 1/1994 | Park et al. |
| 5,306,440 A | 4/1994 | Ripley et al. |
| 5,330,752 A | 7/1994 | Park et al. |
| 5,384,134 A | 1/1995 | Kross et al. |
| 5,409,546 A | 4/1995 | Nakagawa et al. |
| 5,472,703 A | 12/1995 | Vanderlaan et al. |
| 5,607,698 A | 3/1997 | Martin et al. |
| 5,616,568 A | 4/1997 | Pouyani et al. |
| 5,639,481 A | 6/1997 | Kessler et al. |
| 5,725,887 A | 3/1998 | Martin et al. |
| 5,736,165 A | 4/1998 | Ripley |
| 5,782,992 A | 7/1998 | Frangione |
| 5,855,922 A | 1/1999 | Danner |
| 6,033,704 A | 3/2000 | Talley |
| 6,096,328 A | 8/2000 | Sagel et al. |
| 6,488,965 B1 | 12/2002 | Karageozian |
| 6,592,907 B2 | 7/2003 | Karagoezian |

OTHER PUBLICATIONS

Paugh, JR; Brennan, NA; Efron, N.; "Ocular Response to Hydrogen Peroxide"; Abstract of Journal Article printed in American Journal of Optometry and Physiological Optics pp. 91-98; Feb. 1988; 2 Pages.
Doctor FWG et al., "The Math Forum at Drexel." http://mathforum.org/library/drmath/view/56329.html; Jul. 30, 1999; 3 pages.
Dart et. al., in British Journal of Ophthalmology, 1988, 72, 926-930.

\* cited by examiner

*Primary Examiner* — Walter Webb
(74) *Attorney, Agent, or Firm* — Stetina Brunda Garred & Brucker

(57) ABSTRACT

An anti-microbial preservative for use in ophthalmic and dermatologic products. The preservative includes from about 0.005 wt. % to about 0.20 wt. % chlorite compound and from about 0.005 wt. % to about 0.05 wt. % peroxy compound. Additionally, the preservative does not generate chlorine dioxide within the pH range of 5.0-8.8. Also included are an antimicrobial ophthalmic and dermatologic compositions for direct application onto an eye or skin of a living being including from about 0.005 wt. % to about 0.20 wt. % chlorite compound and from about 0.005 wt. % to about 0.05 wt. % peroxy compound. Also included are methods for treating dryness of the eyes and skin disorders (e.g., wounds, burns, infections, ulcerations, psoriasis, etc.) and for disinfecting and cleansing contact lenses while in place upon an eye by applying the composition to the eye or to the contact lens.

9 Claims, 7 Drawing Sheets

SYNERGISTIC ANTIMICROBIAL PREPARATIONS CONTAINING CHLORITE AND HYDROGEN PEROXIDE

CROSS-REFERENCE TO RELATED APPLICATIONS

The present invention is a divisional of U.S. application Ser. No. 13/658,609 filed on Oct. 23, 2012, which is a continuation of U.S. application Ser. No. 12/879,989 filed on Sep. 10, 2010, which is a divisional patent application of U.S. patent application Ser. No. 12/874,443 filed on Sep. 2, 2010, which is a continuation of U.S. patent application Ser. No. 11/633,355 filed on Dec. 4, 2006, which is a continuation-in-part of U.S. patent application Ser. No. 10/614,646 filed on Jul. 7, 2003, which is a continuation-in-part of U.S. patent application Ser. No. 09/911,638 filed Jul. 23, 2001 and matured into U.S. Letters Patent No. 6,592,907 on Jul. 15, 2003, which is a continuation-in-part of U.S. patent application Ser. No. 09/412,174 filed Oct. 4, 1999, the entirety of the disclosures of which are expressly incorporated herein by reference.

STATEMENT RE: FEDERALLY SPONSORED RESEARCH/DEVELOPMENT

Not Applicable

BACKGROUND

1. Field of the Invention

The present invention relates generally to medical compositions and methods, and more particularly to certain disinfectant/antimicrobial preparations and methods for using such preparations i) to disinfect or preserve articles or surfaces, ii) as a topical antiseptic for application to body parts, iii) to prevent or deter scar formation; iv) to treat dermatological disorders such as wounds, burns, ulcers, psoriasis, acne and other scar forming lesions; and v) to treat ophthalmic disorders such as infections, inflammation, dry eye, wound healing, and allergic conjunctivitis.

2. Background of the Invention

A. Antimicrobial and Disinfectant/Antiseptic Agents Used for Disinfection/Antisepsis and Topical Treatment of Wounds, Burns, Abrasions and Infections The prior art has included numerous antimicrobial agents which have purportedly been useable for disinfection of various articles and/or for topical application to a living being for antisepsis and/or treatment of dermal disorders (e.g., wounds, burns, abrasions, infections) wherein it is desirable to prevent or deter microbial growth to aid in healing. Such topical antimicrobial agents have contained a variety of active microbicidal ingredients such as iodine, mercurochrome, hydrogen peroxide, and chlorine dioxide.

i. Prior Chlorine Dioxide Preparations

Chlorite, a precursor of chlorine dioxide, is known to be useable as a disinfectant for drinking water and as a preservative for contact lens care solutions. However, chlorite exhibits only weak microbicidal activity within a concentration range that is acceptable and safe for topical application to the skin (e.g., 50-1000 parts per million). Thus, chlorite has not been routinely used as an active microbicidal ingredient in preparations for topical application to the skin.

In view of the limited usefulness of chlorite as an antiseptic or topical microbicide, various compositions and methods have been proposed for activation or enhancement of the microbicidal activity of chlorite. Examples of such compositions and methods for activation or enhancement of the microbicidal activity of chlorite are described in U.S. Pat. No. 4,997,616 (describing general activation); U.S. Pat. No. 5,279,673 (describing acid activation) and U.S. Pat. No. 5,246,662 (describing transition metal activation).

Chlorine dioxide ($ClO_2$) and "stabilized chlorine dioxide" are known to be useable as antiseptics. Chemically, chlorine dioxide is an oxidizing agent which has strong microbicidal activity. Chlorine dioxide is generally regarded as superior even to gaseous chlorine in certain water treatment applications where it is used as to eliminate algae and other organic material and/or to remove odors or tastes. Chlorine dioxide is also effective as a microbicide, for elimination of bacteria, viruses, and microbial spores.

In addition to its use as a microbicide, chlorine dioxide is a highly reactive, unstable radical which is useable as an oxidizing agent in a number of other chemical and biochemical applications. For example, as described in U.S. Pat. No. 4,855,135, chlorine dioxide can be used for (a) oxidation of double bonds between two carbon atoms; (b) oxidation of unsaturated fatty acids (lipids) via double bonds between two carbon atoms; (c) acceleration of hydrolysis of carboxylic anhydrides; (d) oxidation of aldehydes to the corresponding carboxylic acids; (e) oxidation of alcohols; (f) oxidation of amines; (g) oxidation of phenols, phenolic derivatives and thiophenolic compounds; (h) moderate oxidation of hydroquinones; (i) oxidation of amino acids, proteins and polyamides; j) oxidation of nitrates and sulfides; and (k) alteration of the CHO and $CH_2OH$ radicals of carbohydrates to produce carboxylic functionality.

Concentrated chlorine dioxide in its liquid or gaseous state is highly explosive and poisonous. As a result, concentrated chlorine dioxide must be handled and transported with great caution. For this reason, it is generally not feasible to dispense pure chlorine dioxide for use as a topical antimicrobial agent or disinfectant. Instead, some antimicrobial or disinfectant preparations have been formulated to provide for "acid generation" of chlorine dioxide. Such acid generation solutions contain a metal chlorite (i.e., a precursor of chlorine dioxide available in powdered or liquid form) in combination with an acid which will react with the chlorite to liberate or release chlorine dioxide. Generally, any acid may be used for acid generation of chlorine dioxide, including strong acids such as hydrochloric acid and sulfuric acid and relatively weak acids such as citric and tartaric acid. Drawbacks or problems associated with these prior chlorine dioxide generating systems include a) the inconvenience of handing two separate containers or chemical components, b) the difficulty of delivering such two-component systems to the intended site of application, and c) the fact that these prior systems are of acid, rather than neutral, pH. Moreover, the prior chlorine dioxide generating systems which utilize acid-induced generation of chlorine dioxide can, if uncontrolled, cause the generation of chlorine dioxide to occur quite rapidly and, as a result, the disinfectant or antimicrobial potency of the solution may be short lived. Increasing the concentration of chlorite and acid within the solution may prolong its disinfectant or antimicrobial shelf life, but such increased concentrations of these chemicals can result in toxicities or (in topical applications) skin irritation. Such increased concentrations may also result in the generation of more chlorine dioxide than is required.

Various methods have been described to limit or control the rate at which chlorine dioxide is produced in "acid generation" solutions. For instance, U.S. Pat. No. Re. 31,779 (Alliger), which is a reissue of U.S. Pat. No. 4,084,747, describes a germicidal composition which comprises a water soluble chlorite, such as sodium chlorite, in combination with lactic acid. The particular composition possesses improved disinfectant properties, properties not attained by using the same composition but replacing the lactic acid with other acids such as phosphoric acid, acetic acid, sorbic acid, fumaric acid, sulfamic acid, succinic acid, boric acid, tannic acid, and citric acid. The germ killing composition is produced by contacting an acid material containing at least 15% by weight of lactic acid with sodium chlorite in aqueous media. The methods disclosed of disinfecting and sanitizing a germ-carrying substrate, such as skin, include either application of the germ-killing composition, or application of the reactants to provide in situ production thereof. Also, U.S. Pat. No. 5,384,134 (Kross) describes acid induced generation of chlorine dioxide from a metal chlorite wherein the chlorite concentration is limited by the amount of available chlorous acid. In particular, the Kross patent describes a method for treating dermal disorders wherein a first gel, which comprises a metal chlorite, is mixed with a second gel, which comprises a protic acid. The chlorite ions present in such solution as chlorous acid purportedly comprise no more than about 15% by weight of the total chlorite ion concentration in the composition, and the mixture of the two gels purportedly generates chlorine dioxide over an extended time of up to 24 hours.

Other prior patents have purported to describe the use of "stabilized" chlorine dioxide as a means of chlorine dioxide generation. The term stabilized chlorine dioxide refers to various compositions in which the chlorine dioxide is believed to be held in solution in the form of a labile complex. The stabilization of chlorine dioxide by the use of perborates was disclosed in U.S. Pat. No. 2,701,781 (de Guevara). According to the de Guevara patent, an antiseptic solution of stabilized chlorine dioxide can be formed from an aqueous solution of chlorine dioxide and an inorganic boron compound with the boron compound and the chlorine dioxide being present in the solution as a labile complex. The chlorine dioxide, fixed in this stable condition, is an essential ingredient of the antiseptic solution. The de Guevara patent discloses that the chlorine dioxide may be introduced into the compositions either by in situ generation or it may be generated externally and introduced into the solution, as by bubbling the chlorine dioxide gas into the aqueous solution. Various methods may be employed for the external production of the chlorine dioxide, such as reaction of sulfuric acid with potassium chlorate or the reaction of the chlorate with moist oxalic acid. Alternatively, chlorine dioxide can be generated in situ by reaction of potassium chlorate and sulfuric acid. Note that whether the chlorine dioxide is produced in situ or externally, it is essentially an acid-induced liberation of the chlorine dioxide from potassium chlorate.

U.S. Pat. No. 4,317,814 (Laso) describes stabilized chlorine dioxide preparations for treatment of burns in humans. Aqueous mixtures of perborate stabilized solutions of chlorine oxides, such as chlorine dioxide, in combination with glycerin are described for topical application to burned areas and may also be administered by oral application for treatment of burns. The aqueous solutions of perborate stabilized chlorine oxides are disclosed as being prepared by mixing with water the following: sodium chlorite, sodium hypochlorite, hydrochloric acid, sulfuric acid, an inorganic perborate, and a peroxy compound, such as sodium perborate. Thus, the solutions prepared in accordance with the Laso patent contain chlorine dioxide, hypochlorite and peroxy compounds as strong oxidizing agents and appear to utilize acid activation of the chlorine dioxide. The Laso patent states that the methods disclosed therein resulted in an immediate subsidence of burn related pain in many cases, that healing was rapid and characterized by an absence of infection or contraction, and that the burn scars were smooth and resembled normal tissue, thus eliminating the need for plastic surgery in certain cases. However, long term storage and stability are issues with the aqueous solutions described in the above-identified Laso patent, because such mixtures tend to generate chlorine dioxide very quickly, thus diminishing the long term stability of such mixtures.

U.S. Pat. No. 3,271,242 (McNicholas et al.,) describes stabilized chlorine dioxide solutions which are formed by combining chlorine dioxide gas with an aqueous solution containing a peroxy compound, and subsequently heating the solution to a temperature which is high enough to drive off all free peroxide, but low enough not to destroy the chlorine dioxide. McNicholas et al., states that temperatures "much below" 70 degrees C. are ineffective to drive off the free peroxide in the solution and that temperatures should not exceed 92 degrees C. because at higher temperatures the chlorine dioxide will be driven off. McNicholas further states that, although not "entirely understood," it was believed that heating of the solution to drive off free peroxide was necessary because any free hydrogen peroxide allowed to remain in the solution would release the chlorine dioxide from the solution.

ii. Antibiotic Preparations

Antibiotic compounds have also been commonly used for the therapeutic treatment of burns, wounds, and skin and eye infections. While antibiotics may provide an effective form of treatment, several dangers are often associated with the use of antibiotics in the clinical environment. These dangers may include but are not limited to: (1) changes in the normal flora of the body, with resulting "superinfection" due to overgrowth of antibiotic resistant organisms; (2) direct antibiotic toxicity, particularly with prolonged use which can result in damage to kidneys, liver and neural tissue depending upon the type of antibiotic; (3) development of antibiotic resistant microbial populations which defy further treatment by antibiotics.

B. Difficult-to-Treat Dermal Disorders Other than Wounds, Burns, Abrasions and Infections While even minor wounds and abscesses can be difficult to treat in certain patients and/or under certain conditions, there are well known dermal disorders such as psoriasis and dermal ulcerations, which present particular challenges for successful treatment.

i. Psoriasis

Psoriasis is a noncontagious skin disorder that most commonly appears as inflamed swollen skin lesions covered with silvery white scale. This most common type of psoriasis is called "plaque psoriasis". Psoriasis comes in many different variations and degrees of severity. Different types of psoriasis display characteristics such as pus-like blisters (pustular psoriasis), severe sloughing of the skin (erythrodermic psoriasis), drop-like dots (guttate psoriasis) and smooth inflamed lesions (inverse psoriasis).

The cause of psoriasis is not presently known, though it is generally accepted that it has a genetic component, and it has recently been established that it is an autoimmune skin disorder. Approximately one in three people report a family history of psoriasis, but there is no pattern of inheritance. There are many cases in which children with no apparent family history of the disease will develop psoriasis.

The occurrence of psoriasis in any individual may depend on some precipitating event or "trigger factor". Examples of "trigger factors" believed to affect the occurrence of psoriasis include systemic infections such as strep throat, injury to the skin (the Koebner phenomenon), vaccinations, certain medications, and intramuscular injections or oral steroid medications. Once something triggers a person's genetic tendency to develop psoriasis, it is thought that in turn, the immune system triggers the excessive skin cell reproduction.

Skin cells are programmed to follow two possible programs: normal growth or wound healing. In a normal growth pattern, skin cells are created in the basal cell layer, and then move up through the epidermis to the stratum corneum, the outermost layer of the skin. Dead cells are shed from the skin at about the same rate as new cells are produced, maintaining a balance. This normal process takes about 28 days from cell birth to death. When skin is wounded, a wound healing program is triggered, also known as regenerative maturation. Cells are produced at a much faster rate, theoretically to replace and repair the wound. There is also an increased blood supply and localized inflammation. In many ways, psoriatic skin is similar to skin healing from a wound or reacting to a stimulus such as infection.

Lesional psoriasis is characterized by cell growth in the alternate growth program. Although there is no wound at a psoriatic lesion, skin cells (called "keratinocytes") behave as if there is. These keratinocytes switch from the normal growth program to regenerative maturation. Cells are created and pushed to the surface in as little as 2-4 days, and the skin cannot shed the cells fast enough. The excessive skin cells build up and form elevated, scaly lesions. The white scale (called "plaque") that usually covers the lesion is composed of dead skin cells, and the redness of the lesion is caused by increased blood supply to the area of rapidly dividing skin cells.

Although there is no known cure for psoriasis, various treatments have been demonstrated to provide temporary relief in some patients. However, the effectiveness of the currently accepted treatments for psoriasis is subject to considerable individual variation. As a result, patients and their physicians may have to experiment and/or combine therapies in order to discover the regimen that is most effective. The currently available treatments for psoriasis are often administered in step-wise fashion. Step 1 treatments include a) topical medications (e.g., topical steroids, topical retinoids), b) systemic steroids, c) coal tar, d) anthralin, e) vitamin D3, and sunshine. Step 2 treatments include a) phototherapy (e.g., ultraviolet radiation), b) photochemotherapy (e.g., a combination of a topically applied radiation-activated agent followed by radiation to activate the agent) and c) combination therapy. Step 3 treatments include a) systemic drug therapies such as methotrexate, oral retinoids and cyclosporin and b) rotational therapy.

ii. Dermal Ulcerations

Dermal ulcerations are known to occur as a result of pressure, wear, or primary/secondary vascular disorders. Dermal ulcerations are generally classified according to their etiology, as follows:

a. Decubitus/Pressure Ulcers

A decubitus ulcer or pressure sore is a lesion caused by unrelieved pressure resulting in damage of the underlying tissue. Decubitus ulcers usually develop over a bony prominence such as the elbow or hip. The unrelieved pressure, along with numerous contributing factors, leads to the skin breakdown and persistent ulcerations.

b. Venous Ulcers

Venous ulcers may result from trauma or develop after chronic venous insufficiency (CVI). In CVI, venous valves do not close completely, allowing blood to flow back from the deep venous system through the perforator veins into the superficial venous system. Over time, the weight of this column of blood causes fluid and protein to exude into surrounding tissues, resulting in swollen, hyperpigmented ankles, tissue breakdown, and ulceration. Venous ulcers may be shallow or extend deep into muscle.

c. Arterial Ulcers

Leg ulcers also can develop in patients with arterial insufficiency caused by arterial vessel compression or obstruction, vessel wall changes, or chronic vasoconstriction. Smokers face an especially high risk of arterial disease because nicotine constricts arteries, encourages deposits of atherosclerotic plaque, and exacerbates inflammatory arterial disease (Buerger's disease) and vasoconstrictive disease (Raynaud's disease or phenomenon). Arterial ulcers, caused by trauma to an ischemic limb, can be very painful.

d. Diabetic Ulcers

Arterial insufficiency can be the cause of a nonhealing ulcer in a patient with diabetes. However, most diabetic ulcers result from diabetic neuropathy—because the patient cannot feel pain in his foot, he is unaware of injuries, pressure from too-tight shoes, or repetitive stress that can lead to skin breakdown.

There remains a need in the art for the formulation and development of new disinfectants and topically applicable preparations for the treatment of dermal disorders, such as wounds, burns, abrasions, infections, ulcerations, psoriasis and acne.

C. Contact Lens Soaking and Disinfection.

Whenever a contact lens is removed from an eye, it should be placed in a soaking and disinfecting solution until it is worn again. Soaking and disinfecting solutions have the following functions:

1. Assist in cleaning the lens of ocular secretions after the lens is removed form the eye;
2. To prevent eye infections by a bacterial contaminated lens; and
3. To maintain the state of hydrated equilibrium, which the lens achieves while it is being worn.

D. Contact Lens Cleaning.

During lens wear mucus material, lipids and proteins accumulate on contact lenses, making lens wear uncomfortable due to irritation, burning sensation, and redness. Accordingly, vision becomes blurry. To alleviate the discomforting problem, the soft or rigid contact lenses should be taken out of the eye, to be cleaned and disinfected regularly, using an enzymatic cleaner and a disinfecting solution. One of the serious complications associated with soft lenses can be a Giant Papillary Conjunctivitis (GPC). It is believed to be that the occurrence of the giant papillary conjunctivitis is mostly due to an inflammatory reaction associated with soft contact lens complication. This is almost always caused by protein deposits on contact lenses. GPC produces symptoms ranging from asymptomatic to itching, upper eye-lid edema, red eye, mucoid discharge, progressive contact lens intolerance. The in-the-eye cleaner of the present invention effectively cleans the protein deposits and maintains corneal epithelial cells healthy by keeping the corneal surface from microbial infection as well as by supplying molecular oxygen. Thereby, it provides convenience and benefits to both soft and rigid contact lens wearers.

E. Treatment of Ophthalmic Disorders.

i. Dry Eye

Dry eye is a syndrome in which tear production is inadequate or tear composition is inappropriate to properly wet the cornea and conjunctiva. A variety of disorders of the ocular tears causes sensations of dryness of the eyes, discomfort of presence of a foreign object to occur in the eye. In most instances, the tear film loses its normal continuity and breaks up rapidly so that it cannot maintain its structure during the interval between spontaneous blinks. All of those tear abnormalities may have multiple causes. Perhaps the most common form of dry eye is due to a decreased aqueous component in the tears. Untreated dry eye can be further deteriorated to produce more severe epithelial erosion, strands of epithelial cells, and local dry spots on the cornea, which can be further complicated by microbial infection. In its mild form, however, a feeling of dryness and irritation of the eye can be solved with artificial tears. Thus, artificial tear solution which has a broad spectrum antimicrobial activity with corneal lubricating property, can provide not only comfort but also beneficial effects on recovery of damaged corneal surface.

ii. Allergic Conjunctivitis

Airborne or hand borne allergens usually produce allergic conjunctivitis due to IgE-mediated hypersensitivity reaction. It presents itching, tearing, dry and sticky eyes, including lid-swelling, conjunctival hyperemia, papillary reaction, chemosin, and ropy mucoid discharge. The presence of hyaluronic acid in the tear, which is included in the formulation of artificial tear, would protect corneal surface from contacting the allergens. The broad spectrum antimicrobial agent of the present invention keeps the corneal surface from bacterial infection and also maintains the corneal epithelial cells healthy by supplying molecular oxygen. Thus, it provides beneficial effects on the eyes sensitive to allergens.

iii. Bacterial Invasion

Bacterial keratitis is one of the leading causes of blindness in the world. In the United States, an estimated 30,000 cases occur annually, with the popularity of contact lens wear having contributed to a rising incidence in the developed world. Statistical investigation indicates that about 30 of every 100,000 contact lens wearers develop ulcerative keratitis annually in the United States, thus making the disease a significant public health issue in view of potential blindness that can occur. While eyelids, blinking of the eyelids, and corneal and conjunctival epithelial cells provide barriers to microbial invasion, one or more of these defense mechanisms can become compromised. Such compromises can include lid abnormalities, exposure of the corneal surface, poor tear production, epithelial problems, medication toxicity, trauma, and incisional surgery. Ocular manifestations of bacterial keratitis are found in *staphylococcus* and *streptococcus* infections that tend to cause severe infiltration and necrosis which over time can lead to perforation. Pseudomonal keratitis tends to progress rapidly. This organism produces destructive enzymes, such as protease, lipase, and elastase, and exotoxins, which result in necrotic ulceration and perforation. *Serratia* keratitis starts as a superficial para-central ulcer, with the secretion of exotoxins and protease which can produce aggressive ulceration and perforation. In order for the bacterial keratitis to become established, microbial adhesions must bind to host cell receptors. Once this attachment has occurred, the destructive process of inflammation, necrosis, and angiogenesis can ensue.

Present treatment for bacterial keratitis relies primarily upon the use of broad spectrum antibiotic therapy. Such antibiotics include sulfonamides, trimethaprin, and quinolones. Also included are beta-lactams, penicillins, cephalasporins, aminoglycosides, tetracyclines, chloramphenicol, and erythromycin. While such antibiotics are in wide spread use, they can also become misused where antibiotic resistant pathogens emerge. Additionally, antibiotics only halt the proliferation of bacteria, but do not inhibit the activity of protease enzymes, endotoxins, or exotoxins. As is therefore apparent, a significant need is present for a bactericidal agent that addresses the proliferation of not only bacteria, but also protease enzymes, endotoxins and exotoxins.

BRIEF SUMMARY

The present invention provides antimicrobial preparations (e.g., solutions, gels, ointments, creams, etc.) for disinfection of articles or surfaces (e.g., contact lenses, counter tops, etc.), antisepsis of skin or other body parts, prevention or minimization of scarring, and/or treatment or prophylaxis of dermal (i.e., skin or mucous membrane) disorders (e.g., wounds, burns, infections, cold sores, ulcerations, psoriasis, scar forming lesions, acne), and the treatment of ophthalmic disorders (e.g., infection, inflammation, dry eye, allergic conjunctivitis, and wound healing). The antimicrobial preparations of this invention generally comprise from about 0.001% to about 0.20% by weight of a metal chlorite in combination with from 0.001% to 0.05% of a peroxy compound such as hydrogen peroxide. Additionally, the chlorite/peroxide preparations of the present invention may contain additional components such as polymeric lubricants and surfactants, and/or may be formulated in a polymeric drug delivery system or liposomal preparation. The chlorite/peroxide preparations of the present invention have broad antimicrobial activity, including for example activity against gram negative and gram positive bacteria, yeasts and fungi. Moreover, when applied or administered to treat dermal disorders (e.g., wounds, burns, infections, ulcerations, acne and psoriasis), the chlorite/peroxide preparations of the present invention will not only prevent or lessen microbial infection, but will additionally provide oxygen to the affected tissue, assist in healing and deter scar formation.

Further, in accordance with the invention, there are provided methods for disinfection of items (e.g., contact lenses) and methods for treatment of dermal disorders (e.g., wounds, burns, infections, ulcerations and psoriasis) by application or administration of a chlorite/peroxide preparation of the present invention. With respect to contact lens disinfecting solution, as well as product formulations that will clean contact lenses in the eye without removing the lenses from the eye for cleaning, the concentration of the metal chlorite is between about 0.002% to about 0.20%. With respect to in-eye application, the present bactericidal product is a sterile, isotonic, buffered, clear, colorless solution that additionally contains polymeric lubricant and surfactant. The product has a two-year shelf life when stored in a container (e.g., a white opaque plastic bottle) at room temperature as a stabilized peroxy chloral complex of chlorite and peroxide.

In addition, the invention includes product formulations shown to have efficacy in the treatment of dry eye, wound healing, and allergic conjunctivitis.

Further in accordance with the invention, there are provided methods for deterring scar formation by application or administration of a chlorite/peroxide preparation of the present invention.

Further, in accordance with the invention, there are provided product formulations shown to have supra-additive efficacy in broad spectrum antimicrobial activity.

Furthermore, in accordance with the invention, there are provided methods for deterring eye infections, eye perforations and inflammation by application or administration of a chlorite/peroxide preparation of the present invention.

Further aspects and objects of the present invention will become apparent to those of skill in the art upon reading and understanding of the following detailed description and the examples set forth therein.

DETAILED DESCRIPTION

Figure 1:
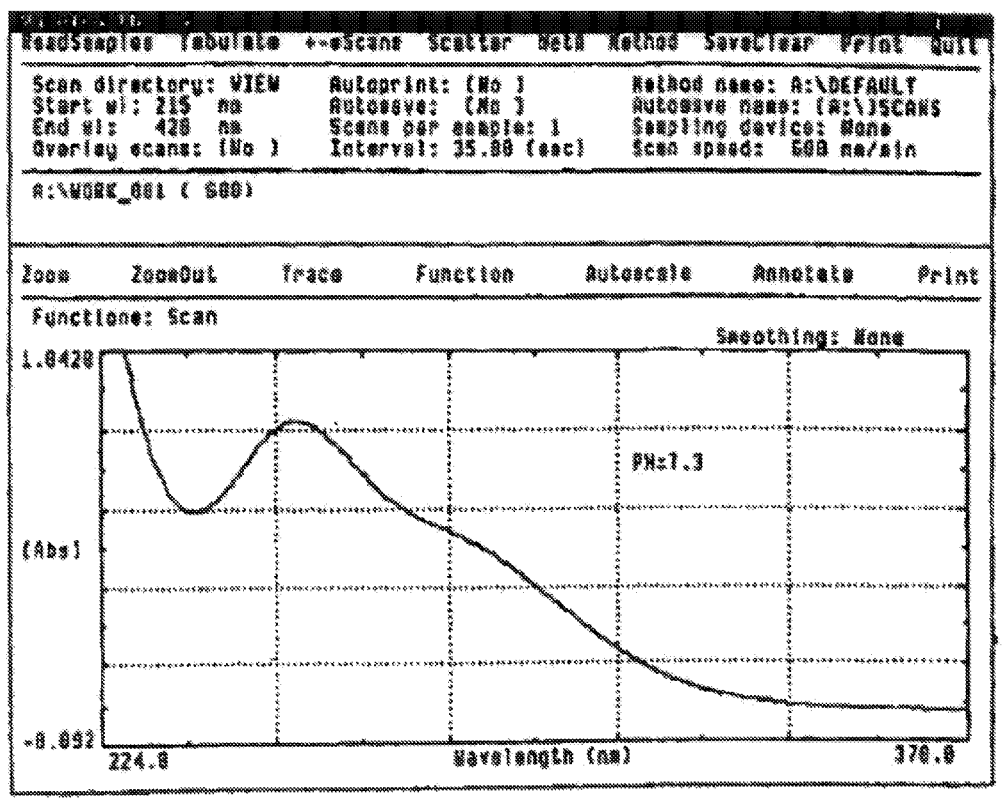
FIG. 1 is a graph demonstrating the non-production of chlorine dioxide at room temperature in the chlorite/peroxide preparation of the present invention at pH level 7.3.

The following detailed description and examples are provided for the purpose of describing certain exemplary embodiments of the invention only, and are not intended to limit the scope of the invention in any way.

The present invention provides preparations which contain chlorite (e.g., a metal chlorite such as sodium chlorite) in combination with a small amount of hydrogen peroxide in neutral aqueous (pH 5.0-8.8, preferably pH 7.0-7.8, and more preferably pH 7.0-7.4) solution. These preparations exhibit synergistic antimicrobial activity without generating chlorine dioxide during storage at room temperature, thereby rendering the stability of these solutions acceptable for pharmaceutical use. For example, an aqueous solution containing 400 ppm chlorite plus 100 ppm hydrogen peroxide remains stable beyond 18 months at room temperature, and is effective to reduce Candida albicans activity by 1.0 log within six hours of challenge, even though the individual components of such solution are ineffective when applied separately at the same concentrations to reduce Candida albicans activity. Additionally, the hydrogen peroxide present within the chlorite/peroxide solutions of the present invention readily decomposes into molecular oxygen and water, upon contact with the peroxidase and catalase enzymes present in tissue and/or some body fluids. Such in situ generation of molecular oxygen contributes to cell vitality and enhances wound healing.

The chlorite/$H_2O_2$ solutions of the present invention are sufficiently stable to be formulated in combination with polymeric lubricants (non-ionic and/or anionic; e.g., HPMC, Methocel, CMC, hyaluronic acid, etc.,) and/or in combination with block polymer based surfactants (e.g., pluronics). For example, an aqueous chlorite/hydrogen peroxide system can be formulated together with methocel or hyaluronic acid as a lubricant and pluronics as a surfactant for contact lens disinfectant solution (viscosity up to 50 cps at 25 degrees C.) in an ophthalmically acceptable tonicity (e.g., osmolality of at least about 200 mOsmol/kg) and a buffer to maintain the pH of the formulation within an acceptable physiological range. The formulation of the contact lens disinfection solution, artificial tear solution, and in-eye cleaner solution, contains chlorite preferably from about 0.005 to about 0.06 weight/volume percent and hydrogen peroxide preferably from about 0.0002 to about 0.05 weight/volume percent. Again, the presence of hydrogen peroxide provides the beneficial oxygen molecule to the cornea upon contact with catalase in the tear.

A. Formulations

The chlorite/peroxide preparations of the present invention may be formulated in various ways, including liquid solutions, gels, ointments, creams, sprays, etc. Set forth herebelow are a few examples of the types of specific formulations which may be prepared in accordance with this invention.

i. Stable Chlorite/Peroxide Liquid Solutions

The following Formula 1 is a first preferred formulation of a liquid chlorite/peroxide solution of the present invention:

| FORMULA 1 | |
|---|---|
| Sodium Chlorite | 0.005%-0.10% |
| Hydrogen Peroxide | 0.005%-0.05% |
| Methocel A | 0.05%-0.2% |
| Boric Acid | 0.15% |
| Sodium Chloride | 0.75% |
| Pluronic F-68/F-127 | 0.1% |
| HCl or NaOH | Adjust pH 7.4 |
| Purified water | Q.S. to volume |

The following Formula 2 is a second preferred formulation of a liquid chlorite/peroxide solution of the present invention:

| FORMULA 2 | |
|---|---|
| Sodium Chlorite | 0.05% |
| Hydrogen Peroxide | 0.02% |
| Carboxymethyl Cellulose | 0.01% |
| Boric Acid | 0.15% |
| Sodium Chloride | 0.75% |
| Pluronic F-68/F-127 | 0.1% |
| HCl or NaOH | Adjust pH 7.3 |
| Purified water | Q.S. to volume |

The chlorite/peroxide solutions of the present invention, such as the solution of the above-shown preferred formulation, may be used for a variety of medical and non-medical applications including but not necessarily limited to a) disinfection of articles and surfaces such as contact lenses, medical/dental instruments, counter tops, treatment tables, combs and brushes, etc.; antisepsis of skin or body parts (e.g., a disinfectant hand wash, antiseptic facial scrub, etc.,) and b) treatment or prophylaxis of dermal (i.e., skin or mucous membrane) disorders such as wounds, burns, infections, ulcerations, cold sores, psoriasis, acne, and c) deterrence or prevention of scar formation, and d) treatment of ophthalmic disorders (e.g., infections or inflammations caused by bacterial keratitis).

As pointed out earlier, the chlorite/hydrogen peroxide system of the present invention is sufficiently stable to be formulated in a polymeric gel form or in a paste form. Furthermore, such polymeric gel or paste formulation can contain polymers which delay or control the release of the chlorite/hydrogen peroxide (e.g., a sustained release delivery system). Such sustained release formulations provide outstanding benefits of increasing therapeutic index by maintaining the effective concentration of chlorite/$H_2O_2$ for a prolonged time on the injured sites, by preventing the injured sites from external microbial contamination by forming a seal over the injured sites, and by providing oxygen molecule to the injured tissues. Unlike the conventional ointment, the polymeric gel provides a dry, clean, and comfortable coating on the injured sites upon application. Such gel formulations may contain polymeric drug delivery vehicles like hydroxypropyl methylcellulose (HPMC), methylcellulase (Methocel), hydroxyethylcellulose (HEC), hyaluronic acid, and carboxymethylcellulose (CMC), etc.

ii. A Stable Chlorite/Peroxide Gel

The following Formula 3 is a presently preferred formulation of a chlorite/peroxide gel of the present invention:

| FORMULA 3 | |
|---|---|
| Sodium Chlorite | 0.02%-0.10% |
| Hydrogen Peroxide | 0.005%-0.05% |
| Methocel A | 2.0% |
| Boric Acid | 0.15% |
| Sodium Chloride | 0.75% |
| Pluronic F-68/F-127 | 0.1% |
| HCl or NaOH | Adjust pH 7.4 |
| Purified water | Q.S. to volume |

Any of the preparations of the present invention may be formulated for sustained release of the active components by forming liposomes of the preparing in accordance with well known liposomal forming techniques and/or by adding to the formulation a pharmaceutically acceptable and effective amount (e.g., typically 1-20 percent by weight) of a sustained release component such as a polymer matrix or one or more of the following:
  a cellulose ester;
  hydroxymethylpropyl cellulose;
  methylhydroxyethyl cellulose;
  hydroxypropyl cellulose;
  hydroxyethyl cellulose;
  carboxymethyl cellulose;
  a salt of a cellulose ester;
  cellulose acetate;
  hydroxypropylmethyl cellulose phthalate;
  methacrylic acid-methyl methacrylate copolymer;
  methacrylic acid-ethyl acetate copolymer;
  polyvinylpyrolidone;
  polyvinyl alcohol;
  hyaluronic acid;
  a phospholipid;
  cholesterol;
  a phospholipid having a neutral charge;
  a phospholipid having a negative charge;
  dipalmytoyl phoshatidyl choline;
  dipalmytoyl phoshatidyl serine; and,
  sodium salts thereof.

iii. A Stable Chlorite/Peroxide Ophthalmic Solution

The following Formula 4 is a presently preferred formulation of a chlorite/peroxide contact lens disinfecting solution for use in cleaning contact lenses residing in or out of the eye. The formulation additionally functions as a tear product for lubrication in dry-eye subjects.

| FORMULA 4 | |
|---|---|
| Sodium Chlorite | 0.002%-0.20% |
| Hydrogen Peroxide | 0.005%-0.05% |
| Hyaluronic Acid | 0.001%-0.50% |
| Boric Acid | 0.15% |
| Sodium Chloride | 0.75% |
| Pluronic 127 | 0.05%-2.0% |
| HCl or NaOH | Adjust pH to 7.4 |
| Purified Water | Q.S. to Volume |

As indicated earlier, the chlorite/peroxide preparation of the present invention, whether it be in the form of liquid solution, gel, ointment, cream, spray, etc., is specifically composed to maintain chlorite such as sodium chlorite and hydrogen peroxide as active ingredients at a pH range of 5.0-8.8 without generating chlorine dioxide during storage at room temperature. By way of illustration, multiple experiments were conducted on the liquid sodium chlorite/hydrogen peroxide solution in accordance with Formula 2 at different levels of pH within the specified range. However, it should be expressly stated herein that such experimentations should in no way be limited to liquid solution forms only, but are performed to illustrate the non-production of chlorine dioxide in the various forms of the present chlorite/peroxide preparation at different pH levels.

The following experimentations were designed to demonstrate the stability of chlorite such as sodium chlorite and hydrogen peroxide antibacterial formulation at neutral, basic and acidic levels of pH. More specifically, the quantitative levels of sodium chlorite and the generation of chlorine dioxide were determined at the pH levels of 7.3, 8.0, 8.8, 7.0, 6.44 and 6.0. 0.1 Normal hydrochloric acid solution and 0.1 Normal sodium hydroxide solution were applied to adjust the pH levels in the experimentations. Sterile 0.9% sodium chloride sterile solution was also applied. A placebo solution with the following formulation was further applied in a spectrophotometer (e.g., Lambda 20 Model UV-Vis. spectrophotometer) to find and measure the levels of sodium chlorite and the generation of chlorine dioxide at varying pH levels:

| Placebo Solution | |
|---|---|
| Hydrogen Peroxide | 0.02% |
| Carboxymethyl Cellulose | 0.01% |
| Boric Acid | 0.15% |
| Sodium Chloride | 0.75% |
| Pluronic F-68/F-127 | 0.1% |
| HCl or NaOH | Adjust pH 7.3 |
| Purified water | Q.S. to volume |

EXPERIMENT 1 pH Level of 7.3

Experiment: Fill the first cuvette with the placebo solution, wipe it clean, and place the cuvette in the standard beam path of the spectrophotometer. Fill the second cuvette with the liquid sodium chlorite/hydrogen peroxide solution, wipe it clean and place the cuvette in the sample beam path of the spectrophotometer. Scan the solutions from 200 nm to 400 nm and record the results. Plot and printout the results, as illustrated in the graph shown in FIG. 1.

Result: The liquid solution contained sodium chlorite and hydrogen peroxide as active ingredients, as well as buffering and tonicity agents at the pH level of 7.3. The placebo solution contained hydrogen peroxide as active ingredient, as well as buffering and tonicity agents at the pH level of 7.3.

Hydrogen peroxide does not absorb in the 200 nm to 400 nm range. Therefore, as seen in FIG. 1, absorption peaks for hydrogen peroxide were not detected.

Sodium chlorite has an absorption maximum at 260 nm, while chlorine dioxide which is a degradation product of sodium chlorite has an absorption maximum at 355 nm-358 nm.

Scanning the solutions that have a pH of 7.3 between the 200 nm and 400 nm will give a quantitative value for sodium chlorite as well as chlorine dioxide in the same scan.

Interpretation: The liquid sodium chlorite/hydrogen peroxide solution does show sodium chlorite peak at 260 nm, but does not show any chlorine dioxide peak at 355 nm-358 nm.

This clearly indicates that at pH level of 7.3, the liquid sodium chlorite/hydrogen peroxide solution has only sodium chlorite, and does not contain any quantities of chlorine dioxide. This is a clear indication that sodium chlorite is stable at pH level of 7.3, and the sodium chlorite is not breaking up and forming the chlorine dioxide.

EXPERIMENT 2 pH Level of 8.0

Experiment: Dispense 25 mL. of the placebo solution and 25 mL. of the liquid sodium chlorite/hydrogen peroxide solution into 2 clean containers. Add 0.1 Normal sodium hydroxide solution to each container so as to adjust the pH of both the placebo solution as well as the liquid solution to a pH level of 8.0.

Fill one of the cuvette with the placebo solution, wipe it clean, and place the cuvette in the standard beam path of the spectrophotometer. Fill the second cuvette with the liquid sodium chlorite/hydrogen peroxide solution, wipe it clean and place the cuvette in the sample beam path of the spectrophotometer. Scan the solutions from 200 nm to 400 nm and record the results. Plot and printout the results, as illustrated in the graph shown in FIG. 2.

Result: The liquid sodium chlorite/hydrogen peroxide solution contained sodium chlorite and hydrogen peroxide as active ingredients, as well as buffering and tonicity agents at the pH level of 8.0. The placebo solution contained hydrogen peroxide as active ingredient, as well as buffering and tonicity agents at the pH level of 8.0.

Figure 2:
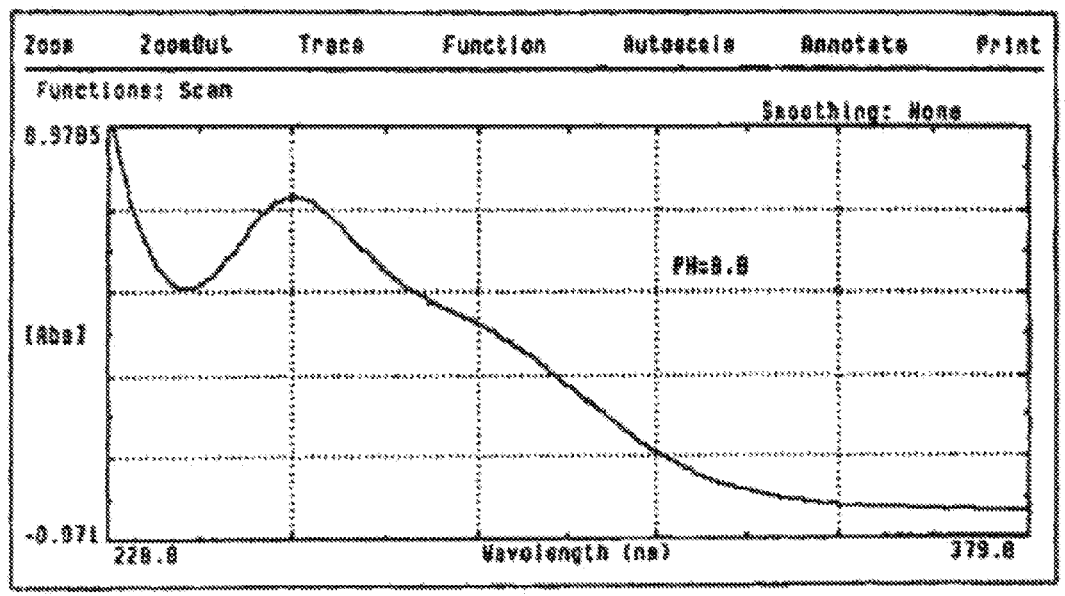
FIG. 2 is a graph demonstrating the non-production of chlorine dioxide at room temperature in the chlorite/peroxide preparation of the present invention at pH level 8.0.

As mentioned shortly above, hydrogen peroxide does not absorb in the 200 nm to 400 nm range. Therefore, as seen in FIG. 2, absorption peaks for hydrogen peroxide were not detected. As also mentioned above, sodium chlorite has an absorption maximum at 260 nm, while chlorine dioxide which is a degradation product of sodium chlorite has an absorption maximum at 355 nm-358 nm.

Scanning the solutions that have a pH level of 8.0 between the 200 nm and 400 nm will give a quantitative value for sodium chlorite as well as chlorine dioxide in the same scan.

Interpretation: The liquid sodium chlorite/hydrogen peroxide solution does show sodium chlorite peak at 260 nm, but does not show any chlorine dioxide peak at 355 nm-358 nm. This clearly indicates that at the pH level of 8.0, the liquid sodium chlorite/hydrogen peroxide solution has only sodium chlorite, and does not contain any quantities of chlorine dioxide. This is a clear indication that sodium chlorite is stable at the pH level of 8.0, and the chlorite is not breaking up and forming chlorine dioxide.

EXPERIMENT 3 pH Level of 8.8

Dispense 25 mL. of the placebo solution and 25 mL. of the liquid sodium chlorite/hydrogen peroxide solution into 2 clean containers. Add 0.1 Normal sodium hydroxide solution to each container so as to adjust the pH of both the placebo solution as well as the liquid solution to a pH level of 8.8.

Fill one of the cuvette with the placebo solution, wipe it clean, and place the cuvette in the standard beam path of the spectrophotometer. Fill the second cuvette with the liquid sodium chlorite/hydrogen peroxide solution, wipe it clean and place the cuvette in the sample beam path of the spectrophotometer. Scan the solutions from 200 nm to 400 nm and record the results. Plot and printout the results, as illustrated in the graph shown in FIG. 3.

Result: The liquid sodium chlorite/hydrogen peroxide solution contained sodium chlorite and hydrogen peroxide as active ingredients, as well as buffering and tonicity agents at the pH level of 8.8. The placebo solution contained hydrogen peroxide as active ingredient, as well as buffering and tonicity agents at the pH level of 8.8.

Figure 3:
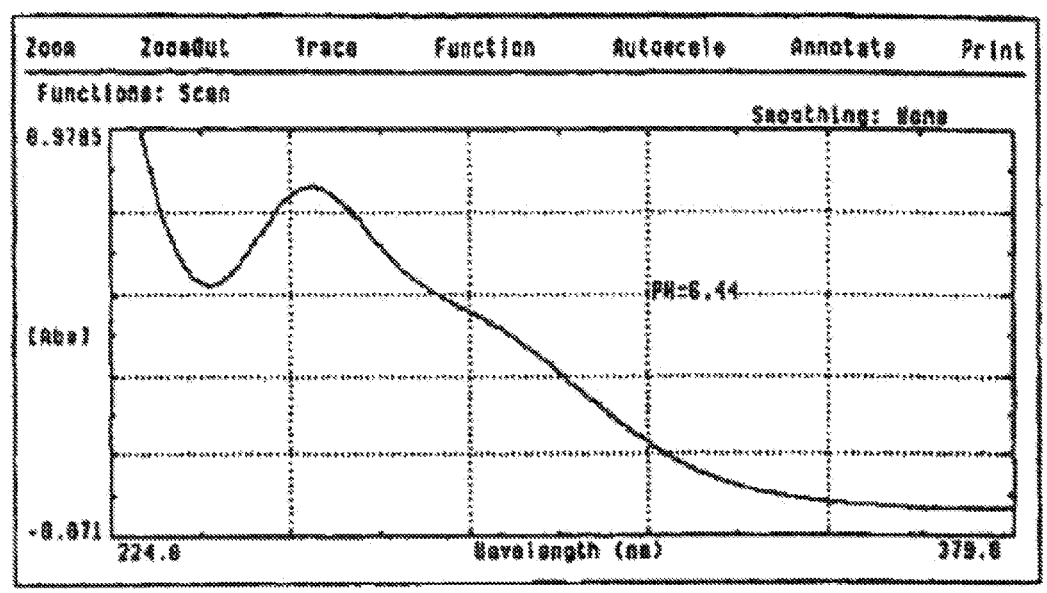
FIG. 3 is a graph demonstrating the non-production of chlorine dioxide at room temperature in the chlorite/peroxide preparation of the present invention at pH level 8.8.

As already discussed, hydrogen peroxide does not absorb in the 200 nm to 400 nm range. Therefore, as seen in FIG. 3, absorption peaks for hydrogen peroxide were not detected. As also discussed, sodium chlorite has an absorption maximum at 260 nm, while chlorine Dioxide which is a degradation product of sodium chlorite has an absorption maximum at 355 nm-358 nm.

Scanning the solutions that have a pH level of 8.8 between the 200 nm and 400 nm will give a quantitative value for sodium chlorite as well as chlorine dioxide in the same scan.

Interpretation: The liquid sodium chlorite/hydrogen peroxide solution does show sodium chlorite peak at 260 nm, but does not show any chlorine dioxide peak at 355 nm-358 nm. This clearly indicates that at the pH level of 8.8, the liquid sodium chlorite/hydrogen peroxide solution has only sodium chlorite, and does not contain any quantities of chlorine dioxide. This is a clear indication that sodium chlorite is stable at the pH level of 8.8, and the chlorite is not breaking up and forming chlorine dioxide.

EXPERIMENT 4 pH Level of 7.0

Experiment: Dispense 25 mL. of the placebo solution and 25 mL. of the liquid sodium chlorite/hydrogen peroxide solution into 2 clean containers. Add 0.1 Normal hydrochloric acid solution to each container so as to adjust the pH of both the placebo solution as well as the liquid solution to a pH level of 7.0.

Fill one of the cuvette with the placebo solution, wipe it clean, and place the cuvette in the standard beam path of the spectrophotometer. Fill the second cuvette with the liquid sodium chlorite/hydrogen peroxide solution, wipe it clean and place the cuvette in the sample beam path of the spectrophotometer. Scan the solutions from 200 nm to 400 nm and record the results. Plot and printout the results, as illustrated in the graph shown in FIG. 4.

Figure 4:
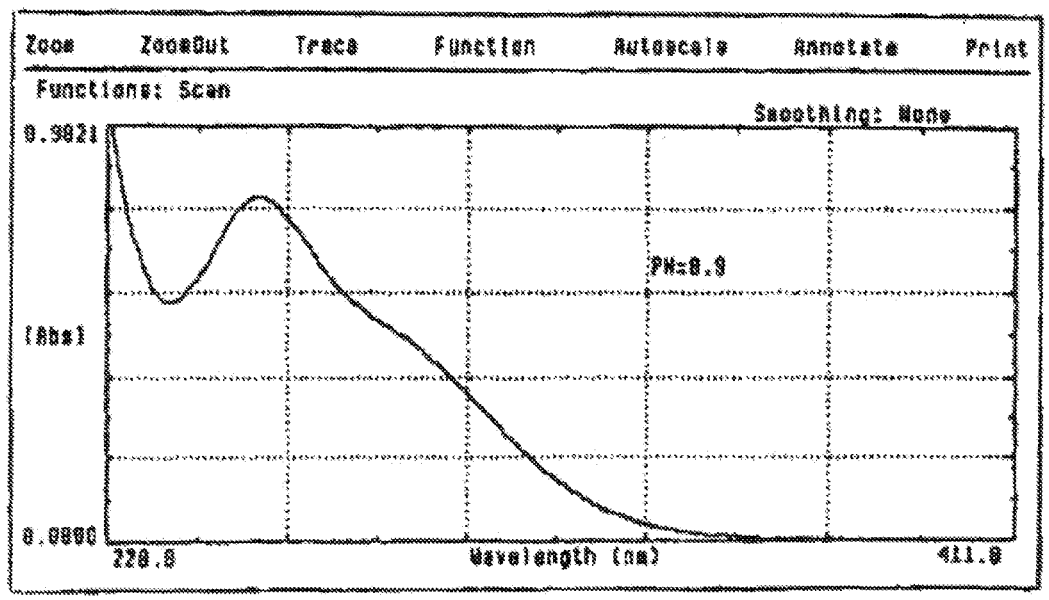
FIG. 4 is a graph demonstrating the non-production of chlorine dioxide at room temperature in the chlorite/peroxide preparation of the present invention at pH level 7.0.

Result: The liquid sodium chlorite/hydrogen peroxide solution contained sodium chlorite and hydrogen peroxide as active ingredients, as well as buffering and tonicity agents at the pH level of 7.0. The placebo solution contained hydrogen peroxide as active ingredient, as well as buffering and tonicity agents at the pH level of 7.0. Hydrogen peroxide does not absorb in the 200 nm to 400 nm range. Therefore, as seen in FIG. 4, absorption peaks for hydrogen peroxide were not detected.

Sodium chlorite has an absorption maximum at 260 nm, while chlorine dioxide which is a degradation product of sodium chlorite has an absorption maximum at 355 nm-358 nm. Scanning the solutions that have a pH of 7.0 between the 200 nm and 400 nm will give a quantitative value for sodium chlorite as well as chlorine dioxide in the same scan.

Interpretation: The sodium chlorite/hydrogen peroxide solution does show sodium chlorite peak at 260 nm, but does not show any chlorine dioxide peak at 355 nm-358 nm. This clearly indicates that at the pH level of 7.0, the liquid solution has only sodium chlorite, and does not contain any quantities of chlorine dioxide. This is a clear indication that sodium chlorite is stable at pH of 7.0, and the chlorite is not breaking up and forming chlorine dioxide.

EXPERIMENT 5 pH Level of 6.44

Experiment: Dispense 25 mL. of the placebo solution and 25 mL. of the liquid sodium chlorite/hydrogen peroxide solution into 2 clean containers. Add 0.1 Normal hydrochloric acid solution to each container so as to adjust the pH of both the placebo solution as well as the liquid solution to a pH level of 6.44.

Figure 5:
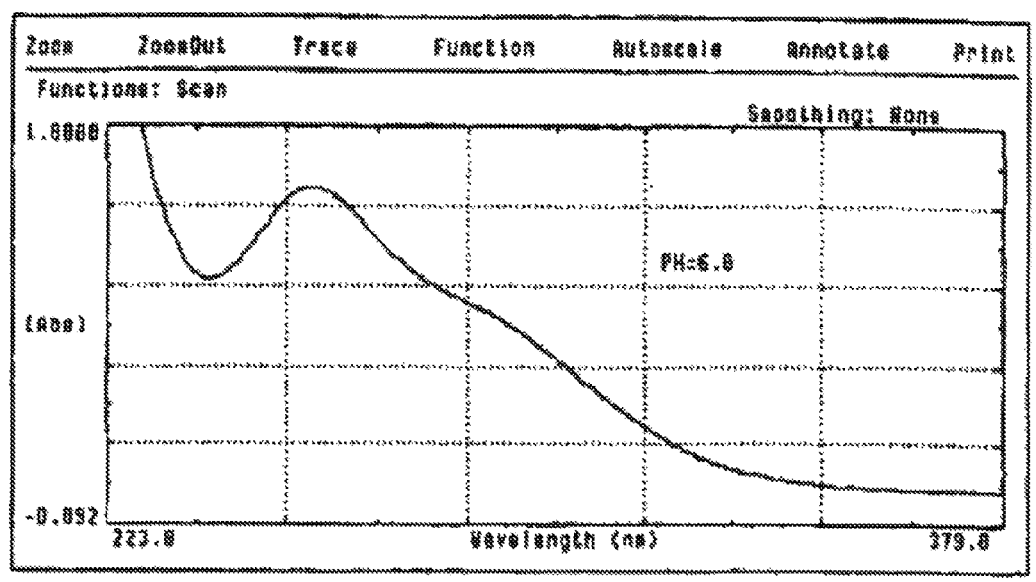
FIG. 5 is a graph demonstrating the non-production of chlorine dioxide at room temperature in the chlorite/peroxide preparation of the present invention at pH level 6.44.

Fill one of the cuvette with the placebo solution, wipe it clean, and place the cuvette in the standard beam path of the spectrophotometer. Fill the second cuvette with the liquid solution, wipe it clean and place the cuvette in the sample beam path of the spectrophotometer. Scan the solutions from 200 nm to 400 nm and record the results. Plot and printout the results, as illustrated in the graph shown in FIG. 5.

Result: The liquid sodium chlorite/hydrogen peroxide solution contained sodium chlorite and hydrogen peroxide as active ingredients, as well as buffering and tonicity agents at the pH level of 6.44.

The placebo solution contained hydrogen peroxide as active ingredient, as well as buffering and tonicity agents at pH=6.44. Hydrogen peroxide does not absorb in the 200 nm to 400 nm range, and thus no absorption peaks for hydrogen peroxide were detected. Sodium chlorite has an absorption maximum at 260 nm, while chlorine dioxide which is a degradation product of sodium chlorite has an absorption maximum at 355 nm-358 nm.

Scanning the solutions that have a pH of 6.44 between the 200 nm and 400 nm will give a quantitative value for sodium chlorite as well as chlorine dioxide in the same scan.

Interpretation: The liquid sodium chlorite/hydrogen peroxide solution does show sodium chlorite peak at 260 nm, but does not show any chlorine dioxide peak at 355 nm-358 nm. This clearly indicates that at pH of 6.44, the liquid solution has only sodium chlorite, and does not contain any quantities of chlorine dioxide. This is a clear indication that sodium chlorite is stable at pH of 6.44, and the chlorite is not breaking up and forming chlorine dioxide.

EXPERIMENT 6 pH Level of 6.0

Experiment: Dispense 25 mL. of the placebo solution and 25 mL. of the liquid sodium chlorite/hydrogen peroxide solution into 2 clean containers. Add 0.1 Normal hydrochloric acid solution to each container so as to adjust the pH of both the placebo solution as well as the liquid solution to a pH level of 6.0.

Fill one of the cuvette with the placebo solution, wipe it clean, and place the cuvette in the standard beam path of the spectrophotometer. Fill the second cuvette with the liquid sodium chlorite/hydrogen peroxide solution, wipe it clean and place the cuvette in the sample beam path of the spectrophotometer. Scan the solutions from 200 nm to 400 nm and record the results. Plot and printout the results, as illustrated in the graph shown in FIG. 6.

Figure 6:
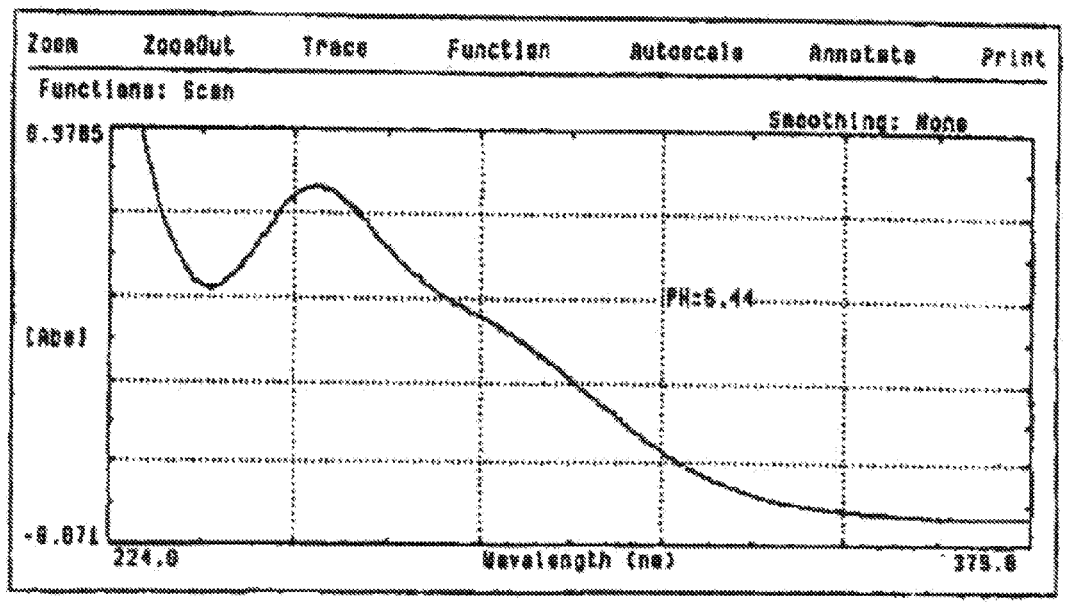
FIG. 6 is a graph demonstrating the non-production of chlorine dioxide at room temperature in the chlorite/peroxide preparation of the present invention at pH level 6.0.

Result: The liquid sodium chlorite/hydrogen peroxide solution contained sodium chlorite and hydrogen peroxide as active ingredients, as well as buffering and tonicity agents at the pH level of 6.0. The placebo solution contained hydrogen peroxide as active ingredient, as well as buffering and tonicity agents at the pH level of 6.0. Hydrogen peroxide does not absorb in the 200 nm to 400 nm range. Therefore, as seen in FIG. 6, absorption peaks for hydrogen peroxide were not detected.

Sodium chlorite has an absorption maximum at 260 nm, while chlorine dioxide which is a degradation product of sodium chlorite has an absorption maximum at 355 nm-358 nm. Scanning the solutions that have a pH of 6.0 between the 200 nm and 400 nm will give a quantitative value for sodium chlorite as well as chlorine dioxide in the same scan.

Interpretation: The sodium chlorite/hydrogen peroxide solution does show sodium chlorite peak at 260 nm, but does not show any chlorine dioxide peak at 355 nm-358 nm. This clearly indicates that at pH level of 6.0, the liquid solution has only sodium chlorite, and does not contain any quantities of chlorine dioxide. This is a clear indication that sodium chlorite is stable at pH of 6.0, and the chlorite is not breaking up and forming chlorine dioxide.

EXPERIMENT 7 pH Level of 1.5

Experiment: Dispense 25 mL. of the placebo solution and 25 mL. of the liquid sodium chlorite/hydrogen peroxide solution into 2 clean containers. Add 0.1 Normal hydrochloric acid solution to each container so as to adjust the pH of both the placebo solution as well as the bactericidal solution to a pH of 1.5.

Figure 7:
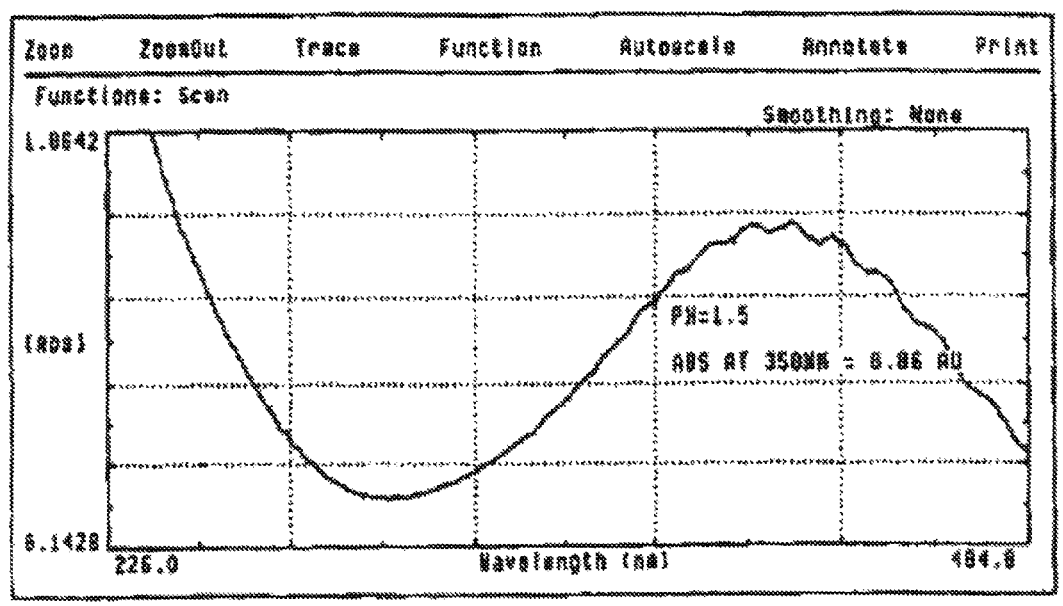
FIG. 7 is a graph demonstrating the production of chlorine dioxide at room temperature in the chlorite/peroxide preparation of the present invention at a pH level of 1.5.

Fill one of the cuvette with the placebo solution, wipe it clean, and place the cuvette in the standard beam path of the spectrophotometer. Fill the second cuvette with the liquid solution, wipe it clean and place the cuvette in the sample beam path of the spectrophotometer. Scan the solutions from 200 nm to 400 nm and record the results. Plot and printout the results, as illustrated in the graph shown in FIG. 7.

Result: The liquid sodium chlorite/hydrogen peroxide solution contained sodium chlorite and hydrogen peroxide as active ingredients, as well as buffering and tonicity agents at pH of 1.5. The placebo solution contained hydrogen peroxide as active ingredient, as well as buffering and tonicity agents at pH of 1.5. As explained earlier, hydrogen peroxide does not absorb in the 200 nm to 400 nm range, and as such, no absorption peaks for hydrogen peroxide were detected.

Also explained earlier, sodium chlorite has an absorption maximum at 260 nm, while chlorine dioxide which is a degradation product of sodium chlorite has an absorption maximum at 355 nm-358 nm. Scanning the solutions that have a pH of 1.5 between the 200 nm and 400 nm will give a quantitative value for sodium chlorite as well as chlorine dioxide in the same scan.

Interpretation: The liquid sodium chlorite/hydrogen peroxide solution does not show sodium chlorite peak at 260 nm, but does show a large chlorine dioxide peak at 355 nm-358 nm. This clearly indicates that at the pH level of 1.5, the liquid sodium chlorite/hydrogen peroxide solution does not have any sodium chlorite. Rather, it clearly shows that the sodium chlorite has been degraded and converted to chlorine dioxide. This is a clear indication that at pH of 1.5, sodium chlorite is very unstable, and all chlorite that is present in the liquid solution is converted to chlorine dioxide.

Results for Experiments 1-7

The liquid sodium chlorite/hydrogen peroxide solution contained sodium chlorite and hydrogen peroxide as active ingredients, as well as buffering and tonicity agents at the pH levels of 1.5, 6.0, 6.44, 7.0, 7.3, 8.0 and 8.8.

The placebo solution contained hydrogen peroxide as active ingredient, as well as buffering and tonicity agents at the pH levels of 1.5, 6.0, 6.44, 7.0, 7.3, 8.0 and 8.8.

Hydrogen peroxide does not absorb in the 200 nm to 400 nm range.

Sodium chlorite has an absorption maximum at 260 nm, while chlorine dioxide has an absorption maximum at 355 nm-358 nm.

Scanning the solutions between the 200 nm and 400 nm gave a quantitative value for sodium chlorite as well as chlorine dioxide in the same scan.

Interpretation of Results for Experiments 1-7

The liquid sodium chlorite/hydrogen peroxide solutions at the pH levels of 6.0, 6.44, 7.0, 7.3, 8.0 and 8.8 does show the presence of sodium chlorite peak at 260 nm, but does not show the presence of chlorine dioxide peak at 355 nm-358 nm.

In contrast, the liquid sodium chlorite/hydrogen peroxide solution at pH of 1.5 does not show the presence of sodium chlorite peak at 260 nm, but does show the presence of chlorine dioxide peak at 355 nm-358 nm.

Conclusion of Results for Experiments 1-7

The results clearly show that one can quantitatively determine the level of sodium chlorite as well as chlorine dioxide which is present in the liquid sodium chlorite/hydrogen peroxide solution at the pH levels of 1.5, 6.0, 6.44, 7.0, 7.3, 8.0 and 8.8.

The results also show that the storage of the liquid sodium chlorite/hydrogen peroxide solution at about room temperature (e.g., in a white opaque bottle exposed to air at room temperature) does not produce any chlorine dioxide as determined by the absence of any absorbance at 355 nm-358 nm.

In conclusion, the results of Experiments 1-7 clearly indicate that the liquid sodium chlorite/hydrogen peroxide solution retains sodium chlorite at the pH range of 6.0-8.8 without the generation of chlorine dioxide. The liquid solution, however, degrades and generates chlorine dioxide upon the acidification of the solution to pH of 1.5. Thus, these results also strongly indicate that the liquid sodium chlorite/hydrogen peroxide solution does not contain chlorine dioxide when it is manufactured, nor does the solution degrade to generate chlorine dioxide after storage at about room temperature at the pH levels of 6.0, 6.44, 7.0, 7.3, 8.0, or 8.8.

Furthermore, these results present clear evidence that the liquid sodium chlorite/hydrogen peroxide solution of the present invention has its bactericidal properties in the pH range studied due to the sodium chlorite/ hydrogen peroxide and not due to chlorine dioxide. This is very much unlike other prior art inventions that have sodium chlorite as a starting material as, but the active bactericide is the chlorine dioxide which is generated by the acidification of the sodium chlorite.

B. EXAMPLES OF THERAPEUTIC APPLICATIONS

The following are specific examples of therapeutic applications of the chlorite/peroxide preparations of the present invention.

i. Example 1

Treatment of Psoriasis-No Crossover

A human patient having psoriasis plaques present on both arms is treated as follows:

Twice daily application to plaques on the left arm only, of a chlorite/peroxide solution having the following formulation:

| | |
|---|---|
| Sodium Chlorite | 0.06% |
| Hydrogen Peroxide | 0.01% |
| HPMC | 2.0% |
| Boric Acid | 0.15% |
| HCl or NaOH | to adjust pH 7.4 |
| Purified water | Q.S. to volume |

Twice daily application to plaques on the right arm only of a commercially available 0.1% triamcinolone acetonide cream.

The chlorite/peroxide treated psoriatic plaques on the right arm began to become less severe within 24 hours of beginning treatment and had substantially disappeared within three days of beginning treatment. However, the triamcinolone acetonide treated psoriatic plaques present on the left arm remained unchanged and inflamed during the two week treatment period.

ii. Example 2

Treatment of Psoriasis-Crossover

A human patient having psoriasis plaques present on both arms is treated for two weeks, as follows:

Twice daily application to plaques on the left arm only, of a chlorite/peroxide solution having the following formulation:

| | |
|---|---|
| Sodium Chlorite | 0.06% |
| Hydrogen Peroxide | 0.01% |
| HPMC | 2.0% |
| Boric Acid | 0.15% |
| HCl or NaOH | to adjust pH 7.4 |
| Purified water | Q.S. to volume/100% |

Twice daily application to plaques on the right arm only of a commercially available 0.1% triamcinolone acetonide cream.

The chlorite/peroxide treated psoriatic plaques on the right arm began to become less severe within 24 hours of beginning treatment and had substantially disappeared within one week of beginning treatment. However, the triamcinolone acetonide treated psoriatic plaques present on the left arm remained unchanged and inflamed during the two week treatment period.

Beginning the day after the end of the initial two week treatment period, and continuing for a second two week treatment period, the patient was treated as follows:

Twice daily application to plaques on the left arm only of the same commercially available 0.1% triamcinolone acetonide cream described hereabove in this example.

Twice daily application to plaques on the right arm only, of the same chlorite/peroxide sustained release gel described hereabove in this example.

Within 24 hours of commencing the second treatment period, the psoriatic lesions on the right arm began to subside. By day three and continuing through the end of the second two week treatment period, the psoriatic lesions on the right arm had substantially disappeared.

iii. Example 3

Treatment of Cold Sores

A patient with painful, fluid-containing cold sores (i.e., chancre sores) on his lips was treated twice daily by application to the lips of a chlorite/peroxide preparation prepared in accordance with Formula 1 above.

Within 6 to 12 hours of the first application of the chlorite/peroxide preparation, the patient reported that the pain had subsided. Within 24 hours of the first application of the chlorite/peroxide preparation, the fluid contained within the cold sores had substantially dissipated and the cold sores appeared dry. Within six days of the first application of the chlorite/peroxide preparation the cold sores had substantially disappeared and the lips appeared normal, whereas cold sores of such severity typically require substantially longer than six days to completely disappear and heal.

iv. Example 4

Treatment of Venous Ulcer

A patient with a venous ulcer on the right leg of 3-4 cm diameter which had been present for 9-12 months was treated by twice daily application to the ulcer of gauze soaked with a chlorite/peroxide liquid solution prepared in accordance with Formula 1 above.

Within three days after commencement of treatment the ulcer appeared clean and dry. Within 14 days of the commencement of treatment the ulcer began to decrease in size and healthy new tissue was observed about its periphery. At 35 days after commencement of treatment, the ulcer had completely healed, without scarring, and the area where the ulcer had been located was free of pain.

v. Example 5

Treatment of Diabetic Decubitus Ulcer

A non-ambulatory, diabetic patient with decubitus ulcers on both legs and some toes, of 12-18 month duration, was treated by daily application of clean, sterile gauze to the ulcers and saturation of each gauze, three times each day, with a liquid chlorite/peroxide solution prepared in accordance with Formula 1 above. Within four to seven days of commencing the chlorite/hydrogen peroxide treatments the ulcers began to appear less inflamed, clean and dry. About seven to ten days after commencement of the chlorite/hydrogen peroxide treatment, granulation tissue began to form within the ulcers. Within 12 to 14 days, re-epithelialization was observed to have begun within the ulcerated areas except for one toe ulcer which had been particularly severe and had permeated to the bone of the toe. Within 30 to 45 days of the commencement of treatment, all of the ulcers except for the severe toe ulcer had completely closed and re-epithelialized, without irregular scar formation. Also, at 30 to 45 days after the commencement of treatment, the toe ulcer had also become substantially smaller (but was not completely closed) and the patient was able to walk. The liquid and or gel formulations of the present invention, such as Formulas 1 and 2 above, may also be applied topically to prevent scar formation due to wounds, burns, acne, infections, trauma, surgical incision, or any other scar-forming lesion or disorder.

vi. Example 6 a. Treatment of Dry Eye Conditions

Subjects with dry eye conditions have itchy and scratchy eyes. In extreme cases, the subjects have more serious problems that can interfere with health maintenance. Subjects were treated with a preferred tear product of the following formulation:

| | |
|---|---|
| Sodium Chlorite | 0.005%-0.02% |
| Hydrogen Peroxide | 0.01% |
| Methylcellulose A4M | 0.075% |

| | |
|---|---|
| Hyaluronic Acid | 0.10%-0.125% |
| Boric Acid | 0.15% |
| Sodium Chloride, USP | 0.75% |
| Pluronic 127 | 0.10% |
| HCl or NaOH | Adjust pH to 7.4 |
| Purified Water | Q.S. to Volume |

Testing of dry eye subjects with rose bengal stain or fluorescein gives a good indication regarding the condition of the corneal epithelial health, while rose bengal staining provides a good indication of the number of dead epithelial cells on the cornea as well as conjunctiva.

Two subjects with dry eye condition were tested with rose bengal stain, and the quantitative staining to the cornea and conjunctiva was documented by photographs. The subjects started using the above preferred tear product at a dosage of two drops three times per day. At the end of two weeks, the two subjects were tested with rose bengal stain and the level of staining was quantitatively documented by photography. The results showed a 50% to 70% reduction in rose bengal staining, which clearly indicates that the preferred tear formulation was ameliorating the corneal and conjunctival cells from dying.

In addition to an objective determination of the health of the epithelial cells, the two subjects were tested subjectively regarding the safety and efficacy of the preferred tear product. First of all, slit-lamp biomicroscopy of the subjects during the two-week treatment period did not show any redness, irritation, inflammation, or other signs of discomfort. Second, the subjects indicated that the application of the tear product completely removed symptoms of redness, itching, scratching, pain, and dryness due to dry eye while providing lubrication that lasted for several hours. It is therefore evident that the tear product exhibits both safety and efficacy in the treatment of dry eye. As is further recognized in view of the foregoing antimicrobial activity of such compositions, the tear product will also have efficacy in enhancing wound healing within the eye such as after surgery where bacterial infections are to be avoided.

b. Treatment of Allergic Conjunctivitis

In addition to treating dry eye condition with the above preferred tear product, the product was also tested in the treatment of conditions from allergic conjunctivitis. In particular, two subjects suffering from allergic conjunctivitis including itchy, scratchy eyes with constant tearing applied two drops of the product three times per day. This dosage resulted in the disappearance of the symptoms.

C. EXAMPLES OF CONTACT LENS CLEANSING i. Example 1

Soaking, Cleaning and Disinfecting

The following formulation is a preferred disinfecting solution applicable to the cleaning of contact lenses by conventional soaking.

| | |
|---|---|
| Sodium Chlorite | 0.05% |
| Hydrogen Peroxide | 0.02% |
| Methylcellulose A4M | 0.075% |
| Hyaluronic Acid | 0.05%-0.10% |
| Boric Acid | 0.15% |
| Pluronic 127 | 0.25%-0.50% |
| Sodium Chloride USP | 0.75% |
| HCl or NaOH | Adjust pH to 7.4 |
| Purified Water | Q.S. to Volume |

Six subjects using soft hydrophilic contact lenses soaked the lenses in the above disinfecting solution and then placed the lenses directly into the eyes. Soaking was performed nightly or on an as-needed basis. All six subjects reported that the lenses felt very comfortable, and that no adverse effects (e.g., burning, stinging, redness, pain) were experienced. Additionally, the solution extended the comfort and clean condition of the lenses for several weeks beyond such extension experienced with other commercially available disinfecting solutions.

The disinfecting solution can be used with soft hydrophilic lenses of varying water content (e.g., 38% to 75%), as well as with silicone acrylate rigid gas permeable lenses. Cycling studies of soft lenses soaked daily in the solution for 30 days showed no damage or change in the physical and chemical characteristics of the lenses. Eye comfort, as earlier noted, is achieved through non-binding and non-accumulating of preservative in soft or rigid gas permeable lenses, while such binding and accumulation can be found in certain currently commercially available formulations to cause irritation and discomfort.

ii. Example 2

Cleaning while Wearing

The following formulation is a preferred disinfecting in-eye solution applicable to the cleaning of contact lenses while they are being worn by introducing the solution into the eye:

| | |
|---|---|
| Sodium Chlorite | 0.02% |
| Hydrogen Peroxide | 0.01%-0.02% |
| Methylcellulose A4M | 0.075% |
| Hyaluronic Acid | 0.075%-0.10% |
| Boric Acid | 0.15% |
| Sodium Chloride USP | 0.75% |
| Pluronic 127 | 0.75% |
| HCl or NaOH | Adjust pH to 7.4 |
| Purified Water | Q.S. to Volume |

Four subjects applied two drops of the above in-eye solution three times per day for 30 days to contact lenses while being worn. Examinations of all of the subjects showed no irritation, burning, stinging, or adverse effects of any kind. These subjects further reported that the solution felt soothing and lubricating.

Two subjects were involved in a comparative study where, first of all, they wore ACUVUE disposable lenses continuously for two weeks with occasional removal and cleaning with commercially available cleaning solutions followed with a saline rinse. After 14 days, the lenses became very gritty and uncomfortable, and were discarded. Second, the two subjects started with new ACUVUE lenses and practiced daily application of the present in-eye solution three times per day without removing or touching the lenses. These subjects were able to wear the lenses for three to four weeks before replacement. Additionally, the inconvenience of cleaning the lenses outside the eye was completely eliminated, as was the risk of lens loss, tearing, or contamination. It is therefore evident that the present in-eye cleaning solution provides cleansing efficacy as well as convenience.

D. In-Vitro And In-Vivo Antimicrobial Efficacy i. Synergistic Activity

Tables I and II compare the antimicrobial effects of (a) 400 ppm sodium chlorite alone; (b) 200 ppm hydrogen peroxide alone; and (c) 400 ppm sodium chlorite and 200 ppm hydrogen peroxide in combination against antibiotic-resistant strains of *staphylococcus haemolyticus* (Table I) and *pseudomonas aeruginosa* (Table II) both isolated from human infected eyes. Tables I and II summarize the antimicrobial effects observed at time points one and two hours after introduction of the test solutions.

TABLE I (*staphylococcus haemolyticus*: Initial inoculum = $1.01 \times 10^7$:Log 7.03)

| Time (hours) | Log Reduction $NaClO_2$ alone (400 ppm) | Log Reduction $H_2O_2$ alone (200 ppm) | $NaClO_2$ & $H_2O_2$ (400 ppm & 200 ppm) |
|---|---|---|---|
| 1 | 0.11 | 0.20 | 0.69 |
| 2 | 1.01 | 0.23 | 2.43 |

TABLE II (*pseudomonas aeruginosa*: Initial inoculum = $2.22 \times 10^6$:Log 6.35)

| Time (hours) | Log Reduction $NaClO_2$ alone (400 ppm) | Log Reduction $H_2O_2$ alone (200 ppm) | $NaClO_2$ & $H_2O_2$ (400 ppm & 200 ppm) |
|---|---|---|---|
| 1 | 0.351 | 0.01 | 0.04 |
| 2 | 1.35 | 0.54 | 6.35 |

In the experiment summarized in Table I, sodium chlorite alone caused a Log reduction in *staphylococcus haemolyticus* bacteria of 0.11 at 1 hour and 1.01 at 2 hours. Hydrogen peroxide alone caused a Log reduction in *staphylococcus haemolyticus* bacteria of 0.20 at 1 hour and 0.23 at 2 hours and the combination of sodium chlorite and hydrogen peroxide caused a Log reduction in *staphylococcus haemolyticus* bacteria of 0.69 at 1 hour and 2.43 at 2 hours. Thus, in this experiment, the antimicrobial effect of the sodium chlorite-hydrogen peroxide combination was significantly greater than the sums of the effects of the sodium chlorite and hydrogen peroxide alone, at least at the 2 hour time point. Accordingly, it is concluded that the sodium chlorite-hydrogen peroxide combination exhibited a supra-additive effect against the strain of *staphylococcus haemolyticus* used in this experiment.

In the experiment summarized in Table II, sodium chlorite along caused a Log reduction in *pseudomonas aeruginosa* bacteria of 0.35 at 1 hour and 1.35 at 2 hours. Hydrogen peroxide alone caused a Log reduction in *pseudomonas aeruginosa* bacteria of 0.01 at 1 hour and 0.54 at 2 hours and the combination of sodium chlorite and hydrogen peroxide caused a Log reduction in *pseudomonas aeruginosa* bacteria 0.04 at 1 hour and 6.35 at 2 hours. Thus, in this experiment, the antimicrobial effect of the sodium chlorite-hydrogen peroxide combination was significantly greater than the sums of the effects of the sodium chlorite and hydrogen peroxide alone, at least in the 2 hour time point. Accordingly, it is concluded that the sodium chlorite-hydrogen peroxide combination exhibited a supra-additive effect against the strain of *pseudomonas aeruginosa* used in this experiment.

ii. Animal Testing

*S. haemolyticus* keratitus was induced in respective right eyes of 12 rabbits by dropping broth containing 50,000 CFU/ml of *S. haemolyticus* onto abraded corneas of these eyes. After 24 hours, all corneas were likewise infected, and the rabbits were divided randomly into three groups. The rabbits (five) of Group I then were treated with the chlorite-hydrogen peroxide formulation defined above as cleaning while wearing contact lenses (here termed "Bactericide"); the rabbits (five) of Group II were treated with commercially available 0.3% ofloxacin antibiotic ophthalmic solution; and the rabbits (two) of Group III were untreated to serve as a control.

At 24 and 48 hours post infection, the rabbits underwent visual eye examination, photographic documentation and biomicroscopy. After 24 hours of treatment, three animals each from Groups I and II and one animal from Group III were sacrificed. The eyes were enucleated and an 8 mm disc of cornea was homogenized and plated onto growth media for microbial isolation and quantification. After 48 hours of treatment, the same procedure was followed for the remaining animals.

Tables III, IV and V summarize the results of this experimentation. As is there apparent, the Bactericide of the present invention exhibited superior overall results as compared to the competing commercially available regimens. The results therefore confirm that the clinical efficacy of the Bactericide is better than the antibiotic treatment. In addition to having excellent bactericidal properties, it is demonstrated that bactericide superiority is probably attributable to inactivation of bacterial proteolytic enzymes (thus decreasing bacterial virulence) and inactivation of bacterial toxins responsible for inflammation and hyperemia.

TABLE III

IN-VIVO ANTIMICROBIAL EFFICACY IN INFECTIOUS *S. HAEMOLYTICUS* KERATITIS IN RABBITS

| Post Treatment Time | Group I Bactericide | | Group II 0.3% Ofloxacin | | Group III Untreated Control |
|---|---|---|---|---|---|
| 24 hours | i) | 0 CFU | i) | 23,000 CFU | 39,000 CFU |
| | ii) | 18,000 CFU | ii) | 5,000 CFU | |
| | iii) | 0 CFU | iii) | 11,000 CFU | |
| Average | | 6,000 CFU | | 13,000 CFU | 39,000 CFU |
| 48 hours | i) | 0 CFU | i) | 5,000 CFU | 231,000 CFU |
| | ii) | 0 CFU | ii) | 5,200 CFU | |
| Average | | 0 CFU | | 5,100 CFU | 231,000 CFU |

TABLE IV

IN-VIVO CLINICAL EFFICACY IN INFECTIOUS *S. HAEMOLYTICUS* KERATITIS IN RABBITS

| Time | Group I Bactericide | Group II 0.3% Ofloxacin | Group III Untreated Control |
|---|---|---|---|
| 24 hours after infection | inflammation (+2) hyperemia (+2) corneal edema (+2) | inflammation(+2) hyperemia (+2) corneal edema (+2) | inflammation(+2) hyperemia (+2) corneal edema (+2) |
| 24 hours after treatment | inflammation (0) hyperemia (0) corneal edema (0) | inflammation(+2) hyperemia (+2) corneal edema (+2) | inflammation(+3) hyperemia (+3) corneal edema (+3) |

TABLE IV-continued

IN-VIVO CLINICAL EFFICACY IN INFECTIOUS
*S. HAEMOLYTICUS* KERATITIS IN RABBITS

| Time | Group I Bactericide | Group II 0.3% Ofloxacin | Group III Untreated Control |
|---|---|---|---|
| 48 hours after treatment | inflammation (0) hyperemia (0) corneal edema (0) | inflammation(+1) hyperemia (+1) corneal edema (+1) | inflammation(+3) hyperemia (+3) corneal edema (+3) |

TABLE V

IN-VITRO INHIBITION OF PROTEOLYTIC ENZYME ACTIVITY
Inhibition of proteolytic enzyme activity of
Trypsin and porcine pancreatic Elastase

| Enzyme | Concentration of Bactericide | % Inhibition of Enzyme activity |
|---|---|---|
| Elastase (porcine) | 0.18 ppm | 46% |
| Trypsin | 0.12 ppm | 28% |

E. Ocular Tolerability And Degradation Speed i. Ocular Tolerability of High Levels of Hydrogen Peroxide Previously, it was believed that the upper limit of human ocular tolerability of hydrogen peroxide is about 100 ppm (0.01 wt. %). See Paugh, J. R., Brennan, N. A., and Efron, N., *Ocular Response to Hydrogen Peroxide*, Am. J. Optom. Physiol. Opt. 1988 February; 65(2):91-8. The following experiments show, however, that when combined with sodium chlorite, hydrogen peroxide is well tolerated by human eyes in levels up to 500 ppm (0.05 wt. %). In all of the following experiments, the hydrogen peroxide was combined with 400 ppm (0.04 wt. %) of sodium chlorite in 0.2% boric acid at pH 7.4 and filtered through a 0.2 μm Acrodisc syringe filter. Two drops of each formulation were then placed in the cul-de-sac of two normal human eyes. Upon instillation of the drops, the subjects were instructed to close their eyelids. The subjects' ocular symptoms of the treated eyes were observed and graded over a period of one hour post instillation, for burning and stinging sensation, pain, redness, tearing, itching, photopsia, photophobia, discharge, and foreign body sensation. The observations are presented below.

TABLE VI

Experiment 1: Human Ocular Response to 100 ppm of Hydrogen Peroxide

| | Time post instillation | | | | | | |
|---|---|---|---|---|---|---|---|
| | Zero time | 30 seconds | 1 minute | 2 minutes | 3 minutes | 5 minutes | 10 minutes | 60 minutes |
| Burning/Stinging | 0 | 0 | 0 | 0 | 0 | 0 | 0 | 0 |
| Pain | 0 | 0 | 0 | 0 | 0 | 0 | 0 | 0 |
| Redness | 0 | 0 | 0 | 0 | 0 | 0 | 0 | 0 |
| Tearing | 0 | 0 | 0 | 0 | 0 | 0 | 0 | 0 |
| Itching | 0 | 0 | 0 | 0 | 0 | 0 | 0 | 0 |
| Photopsia | 0 | 0 | 0 | 0 | 0 | 0 | 0 | 0 |
| Photophobia | 0 | 0 | 0 | 0 | 0 | 0 | 0 | 0 |
| Discharge | 0 | 0 | 0 | 0 | 0 | 0 | 0 | 0 |
| Foreign body sensation | 0 | 0 | 0 | 0 | 0 | 0 | 0 | 0 |

Grading Scale: 0 = None; +0.5 = Trace; +1 = Mild; +2 = Moderate; +3 = Moderately Severe; +4 = Severe

TABLE VII

Experiment 2: Human Ocular Response to 200 ppm of Hydrogen Peroxide

| | Time post instillation | | | | | | |
|---|---|---|---|---|---|---|---|
| | Zero time | 30 seconds | 1 minute | 2 minutes | 3 minutes | 5 minutes | 10 minutes | 60 minutes |
| Burning/Stinging | 0 | 0 | 0 | 0 | 0 | 0 | 0 | 0 |
| Pain | 0 | 0 | 0 | 0 | 0 | 0 | 0 | 0 |
| Redness | 0 | 0 | 0 | 0 | 0 | 0 | 0 | 0 |
| Tearing | 0 | 0 | 0 | 0 | 0 | 0 | 0 | 0 |
| Itching | 0 | 0 | 0 | 0 | 0 | 0 | 0 | 0 |
| Photopsia | 0 | 0 | 0 | 0 | 0 | 0 | 0 | 0 |
| Photophobia | 0 | 0 | 0 | 0 | 0 | 0 | 0 | 0 |
| Discharge | 0 | 0 | 0 | 0 | 0 | 0 | 0 | 0 |
| Foreign body sensation | 0 | 0 | 0 | 0 | 0 | 0 | 0 | 0 |

Grading Scale: 0 = None; +0.5 = Trace; +1 = Mild; +2 = Moderate; +3 = Moderately Severe; +4 = Severe

TABLE VIII

Experiment 3: Human Ocular Response to 300 ppm of Hydrogen Peroxide

| | Time post instillation | | | | | | | |
|---|---|---|---|---|---|---|---|---|
| | Zero time | 30 seconds | 1 minute | 2 minutes | 3 minutes | 5 minutes | 10 minutes | 60 minutes |
| Burning/Stinging | 0 | 0 | 0 | 0 | 0 | 0 | 0 | 0 |
| Pain | 0 | 0 | 0 | 0 | 0 | 0 | 0 | 0 |
| Redness | 0 | 0 | 0 | 0 | 0 | 0 | 0 | 0 |
| Tearing | 0 | 0 | 0 | 0 | 0 | 0 | 0 | 0 |
| Itching | 0 | 0 | 0 | 0 | 0 | 0 | 0 | 0 |
| Photopsia | 0 | 0 | 0 | 0 | 0 | 0 | 0 | 0 |
| Photophobia | 0 | 0 | 0 | 0 | 0 | 0 | 0 | 0 |
| Discharge | 0 | 0 | 0 | 0 | 0 | 0 | 0 | 0 |
| Foreign body sensation | 0 | 0 | 0 | 0 | 0 | 0 | 0 | 0 |

Grading Scale: 0 = None; +0.5 = Trace; +1 = Mild; +2 = Moderate; +3 = Moderately Severe; +4 = Severe

TABLE IX

Experiment 4: Human Ocular Response to 400 ppm of Hydrogen Peroxide

| | Time post instillation | | | | | | | |
|---|---|---|---|---|---|---|---|---|
| | Zero time | 30 seconds | 1 minute | 2 minutes | 3 minutes | 5 minutes | 10 minutes | 60 minutes |
| Burning/Stinging | 0 | 0 | 0 | 0 | 0 | 0 | 0 | 0 |
| Pain | 0 | 0 | 0 | 0 | 0 | 0 | 0 | 0 |
| Redness | 0 | 0 | 0 | 0 | 0 | 0 | 0 | 0 |
| Tearing | 0 | 0 | 0 | 0 | 0 | 0 | 0 | 0 |
| Itching | 0 | 0 | 0 | 0 | 0 | 0 | 0 | 0 |
| Photopsia | 0 | 0 | 0 | 0 | 0 | 0 | 0 | 0 |
| Photophobia | 0 | 0 | 0 | 0 | 0 | 0 | 0 | 0 |
| Discharge | 0 | 0 | 0 | 0 | 0 | 0 | 0 | 0 |
| Foreign body sensation | 0 | 0 | 0 | 0 | 0 | 0 | 0 | 0 |

Grading Scale: 0 = None; +0.5 = Trace; +1 = Mild; +2 = Moderate; +3 = Moderately Severe; +4 = Severe

TABLE X

Experiment 5: Human Ocular Response to 500 ppm of Hydrogen Peroxide

| | Time post instillation | | | | | | | |
|---|---|---|---|---|---|---|---|---|
| | Zero time | 30 seconds | 1 minute | 2 minutes | 3 minutes | 5 minutes | 10 minutes | 60 minutes |
| Burning/Stinging | 0 | 0 | 0 | 0 | 0 | 0 | 0 | 0 |
| Pain | 0 | 0 | 0 | 0 | 0 | 0 | 0 | 0 |
| Redness | 0 | 0 | 0 | 0 | 0 | 0 | 0 | 0 |
| Tearing | 0 | 0 | 0 | 0 | 0 | 0 | 0 | 0 |
| Itching | 0 | 0 | 0 | 0 | 0 | 0 | 0 | 0 |
| Photopsia | 0 | 0 | 0 | 0 | 0 | 0 | 0 | 0 |
| Photophobia | 0 | 0 | 0 | 0 | 0 | 0 | 0 | 0 |
| Discharge | 0 | 0 | 0 | 0 | 0 | 0 | 0 | 0 |
| Foreign body sensation | 0 | 0 | 0 | 0 | 0 | 0 | 0 | 0 |

Grading Scale: 0 = None; +0.5 = Trace; +1 = Mild; +2 = Moderate; +3 = Moderately Severe; +4 = Severe As can be seen from the above data, hydrogen peroxide levels up to 500 ppm are very well tolerated by human eyes when in the presence of sodium chlorite. There were no signs of irritation, inflammation, or any other adverse effects associated with the instillation of the formulations containing up to 500 ppm hydrogen peroxide. These results show that hydrogen peroxide up to 500 ppm can be very safe and free of any adverse effects to the human eye when used in conjunction with sodium chlorite. Furthermore as discussed above, an outstanding synergistic antimicrobial activity has been discovered with formulations containing sodium chlorite and hydrogen peroxide. Because the previous literature (See Paugh) reported that human ocular tolerability of hydrogen peroxide is about 100 ppm, it is believed that the sodium chlorite must be stabilizing the hydrogen peroxide by forming a kind of transient complex molecule (e.g., peroxychlorite), which exhibits the excellent synergistic antimicrobial activity and degrades to innocuous products like water, oxygen, and salt upon contact with biological systems, as will be discussed in greater detail below.

ii. Hydrogen Peroxide/Sodium Chlorite Degradation in the Eye

The following experiments were designed to determine the speed of self degradation of the hydrogen peroxide/sodium chlorite formulation when placed in the human eye and to determine the level of ocular symptomatology associated with the formulation when used in an "in the eye" contact lens cleaner product or an artificial tear product.

Experiment 1

"In the Eye" Contact Lens Cleaner

An "in the eye" contact lens cleaner containing 0.5 g carboxymethylcellulose, 0.5 g pluronic, and 0.05 g hydrogen peroxide/sodium chlorite mixture in 100 mL sterile water was provided. The cleaner contained 400 ppm sodium chlorite and 100 ppm hydrogen peroxide for a total of 500 ppm hydrogen peroxide/sodium chlorite mixture. Two drops of the cleaner were placed in the cul-de-sac of two normal human eyes. Upon instillation of the drops, the subjects closed their eyelids and pressed their index finger on the medial cantus, so as to block the puncta and stop the tears going into the lachrymal duct.

At 30 second, 1 minute, 2 minute, and 3 minute intervals, the subjects' tear samples were obtained by placing a fresh peroxide test strip in the cul-de-sac of the subjects' eyes. The used peroxide test strips were removed from the eye and left to dry at room temperature for 15 minutes. At the completion of the drying period, the level of hydrogen peroxide/sodium chlorite material left in the tear was estimated by comparing the color formed on the peroxide test strip to that of a standard color chart and recorded as shown below.

TABLE XI

|  | Time post instillation | | | | |
| --- | --- | --- | --- | --- | --- |
|  | Zero time | 30 seconds | 1 minute | 2 minutes | 3 minutes |
| Level of hydrogen peroxide/sodium chlorite | 500 ppm | >25 ppm | 10 ppm | 2 ppm | 0.5 ppm |

The data presented above shows a rapid reduction in the level of hydrogen peroxide/sodium chlorite in the tear film of the treated subjects. The placing of the index finger on the medial cantus blocks the puncta and does not allow the tears of the subjects to escape into the lachrymal duct. In addition, the closing off the eyelids stops the blinking process and thus stops the pumping action of the tear removal from the treated eyes. As such, it would appear that the rapid reduction in the level of hydrogen peroxide/sodium chlorite from the tears is not due to the loss of the tears of the subjects into the lachrymal duct. Rather, it is believed that the reduction is due to the presence of catalase and superoxide desmutase enzymes in the tears of human subjects. As the drops are placed in the eye of the patients, the catalase and other enzymes start the rapid enzymatic degradation of the hydrogen peroxide/sodium chlorite preparation, whereby in a matter of 3 minutes the level in the tears of the treated subjects is almost undetectable. The results of this experiment tend to show that upon instillation in the eye, the hydrogen peroxide/sodium chlorite mixture behaves like a self destructing preservative with the end products being water, oxygen, and sodium chloride.

Additionally, the ocular symptoms of the treated eyes were observed and graded over a period of one hour post instillation for burning and stinging sensations, pain, redness, tearing, itching, photopsia, photophobia, discharge and for foreign body sensation as shown below.

TABLE XII

|  | Time post instillation | | | | | | | | |
| --- | --- | --- | --- | --- | --- | --- | --- | --- | --- |
|  | Zero time | 30 seconds | 1 minute | 2 minutes | 3 minutes | 5 minutes | 10 minutes | 15 minutes | 30 minutes | 60 minutes |
| Burning/Stinging | 0 | 0 | 0 | 0 | 0 | 0 | 0 | 0 | 0 | 0 |
| Pain | 0 | 0 | 0 | 0 | 0 | 0 | 0 | 0 | 0 | 0 |
| Redness | 0 | 0 | 0 | 0 | 0 | 0 | 0 | 0 | 0 | 0 |
| Tearing | 0 | 0 | 0 | 0 | 0 | 0 | 0 | 0 | 0 | 0 |
| Itching | 0 | 0 | 0 | 0 | 0 | 0 | 0 | 0 | 0 | 0 |
| Photopsia | 0 | 0 | 0 | 0 | 0 | 0 | 0 | 0 | 0 | 0 |
| Photophobia | 0 | 0 | 0 | 0 | 0 | 0 | 0 | 0 | 0 | 0 |
| Discharge | 0 | 0 | 0 | 0 | 0 | 0 | 0 | 0 | 0 | 0 |
| Foreign Body Sensation | 0 | +0.5 | 0 | 0 | 0 | 0 | 0 | 0 | 0 | 0 |

Grading Scale: 0 = None; +0.5 = Trace; +1 = Mild; +2 = Moderate; +3 = Moderately Severe; +4 = Severe The above results show that the hydrogen peroxide/sodium chlorite mixture is very well tolerated by the human eye without presenting any signs of irritation, inflammation, or any other adverse effects.

Experiment 2

Artificial Tear Product

An artificial tear product containing 0.15 g sodium hyaluronate, 0.50 g protector, and 0.06 g hydrogen peroxide/sodium chlorite mixture in 100 mL sterile water was provided. The artificial tear product contained 400 ppm sodium chlorite and 200 ppm hydrogen peroxide for a total of 600 ppm hydrogen peroxide/sodium chlorite mixture. Two drops of the cleaner were placed in the cul-de-sac of six normal human eyes. Upon instillation of the drops, the subjects closed their eyelids and pressed their index finger on the medial cantus, so as to block the puncta and stop the tears going into the lachrymal duct.

At zero second, 5 second, 20 second, 30 second, 60 second, 90 second, 120 second, and 180 second intervals, the subjects' tear samples were obtained by placing a fresh peroxide test strip in the cul-de-sac of the subjects' eyes. The used peroxide test strips were removed from the eye and left to dry at room temperature for 15 minutes. At the completion of the drying period, the level of hydrogen peroxide/sodium chlorite material left in the tear was estimated by comparing the color formed on the peroxide test strip to that of a standard color chart and recorded as shown below.

TABLE XIII

| | Time post instillation | | | | | | | |
|---|---|---|---|---|---|---|---|---|
| | Time 0 | 5 seconds | 20 seconds | 30 seconds | 60 seconds | 90 seconds | 120 seconds | 180 seconds |
| Subject 1 | | | 150 ppm | 60 ppm | 45 ppm | 38 ppm | | |
| Subject 2 | | | | 75 ppm | 38 ppm | 38 ppm | 23 ppm | |
| Subject 3 | | | | | 45 ppm | 30 ppm | 8 ppm | 15 ppm |
| Subject 4 | | | 60 ppm | | | 15 ppm | 11 ppm | 15 ppm |
| Subject 5 | | | 60 ppm | 23 ppm | | | | 5 ppm |
| Subject 6 | | | 150 ppm | 75 ppm | 30 ppm | | 17 ppm | |
| Average | 600 ppm | 375 ppm | 105 ppm | 58 ppm | 40 ppm | 30 ppm | 15 ppm | 12 ppm |

The data presented above shows a rapid reduction in the level of hydrogen peroxide/sodium chlorite in the tear film of the treated subjects. The placing of the index finger on the medial cantus blocks the puncta and does not allow the tears of the subjects to escape into the lachrymal duct. In addition, the closing off the eyelids stops the blinking process and thus stops the pumping action of the tear removal from the treated eyes. As such, it would appear that the rapid reduction in the level of hydrogen peroxide/sodium chlorite from the tears is not due to the loss of the tears of the subjects into the lachrymal duct. Rather, it is believed that the reduction is due to the presence of catalase and superoxide desmutase enzymes in the tears of human subjects. As the drops are placed in the eye of the patients, the catalase and other enzymes start the rapid enzymatic degradation of the hydrogen peroxide/sodium chlorite preparation, whereby in a matter of 3 minutes the level in the tears of the treated subjects is almost undetectable. The results of this experiment tend to show that upon instillation in the eye, the hydrogen peroxide/sodium chlorite mixture behaves like a self destructing preservative with the end products being water, oxygen, and sodium chloride.

Additionally, the ocular symptoms of the treated eyes were observed and graded over a period of one hour post instillation for burning and stinging sensations, pain, redness, tearing, itching, photopsia, photophobia, discharge and for foreign body sensation as shown below.

TABLE XIV

| | Time post instillation | | | | | | | | |
|---|---|---|---|---|---|---|---|---|---|
| | Zero time | 30 seconds | 1 minute | 2 minutes | 3 minutes | 5 minutes | 10 minutes | 15 minutes | 30 minutes | 60 minutes |
| Burning/Stinging | 0 | 0 | 0 | 0 | 0 | 0 | 0 | 0 | 0 | 0 |
| Pain | 0 | 0 | 0 | 0 | 0 | 0 | 0 | 0 | 0 | 0 |
| Redness | 0 | 0 | 0 | 0 | 0 | 0 | 0 | 0 | 0 | 0 |
| Tearing | 0 | 0 | 0 | 0 | 0 | 0 | 0 | 0 | 0 | 0 |
| Itching | 0 | 0 | 0 | 0 | 0 | 0 | 0 | 0 | 0 | 0 |
| Photopsia | 0 | 0 | 0 | 0 | 0 | 0 | 0 | 0 | 0 | 0 |
| Photophobia | 0 | 0 | 0 | 0 | 0 | 0 | 0 | 0 | 0 | 0 |
| Discharge | 0 | 0 | 0 | 0 | 0 | 0 | 0 | 0 | 0 | 0 |
| Foreign Body Sensation | 0 | +0.5 | 0 | 0 | 0 | 0 | 0 | 0 | 0 | 0 |

Grading Scale: 0 = None; +0.5 = Trace; +1 = Mild; +2 = Moderate; +3 = Moderately Severe; +4 = Severe The above results show that the hydrogen peroxide/sodium chlorite mixture is very well tolerated by the human eye without presenting any signs of irritation, inflammation, or any other adverse effects.

It will be appreciated by those skilled in the art, that the invention has been described hereabove with reference to certain examples and specific embodiments. However, these are not the only examples and embodiments in which the invention may be practiced. Indeed, various modifications may be made to the above-described examples and embodiments without departing from the intended spirit and scope of the present invention. Accordingly, the present embodiments are to be considered on all respects as illustrative and not restrictive. It is intended that all such modifications be included within the scope of the following claims.

What is claimed is:

1. An anti-microbial preservative for use in an ophthalmic product, the preservative consisting of from about 0.005 wt. % to about 0.20 wt. % chlorite compound and from about 0.005 wt. % to about 0.05 wt % peroxy compound, wherein the preservative does not contain chlorine dioxide prior to application to the eye of an individual, and wherein the preservative is at a pH range between about 6.0 and about 8.8.

2. The preservative of claim 1 wherein the chlorite compound is a metal chlorite.

3. The preservative of claim 2 wherein the metal is sodium.

4. The preservative of claim 2 wherein the metal is selected from the group consisting of potassium, calcium, and magnesium.

5. The preservative of claim 1 wherein the peroxy compound is hydrogen peroxide.

6. The preservative of claim 1 wherein the ophthalmic product is an artificial tear solution.

7. The preservative of claim 1 wherein the ophthalmic product is a contact lens disinfecting solution.

8. The preservative of claim 1 wherein the ophthalmic product is a contact lens cleaning solution.

9. The preservative of claim 8 wherein the cleaning solution is directly applied to a contact lens in place on an eye of a living being.

* * * * *